United States Patent [19]

Schwartz

[11] Patent Number: 5,632,745
[45] Date of Patent: May 27, 1997

[54] SURGICAL IMPLANTATION OF CARTILAGE REPAIR UNIT

[75] Inventor: Robert E. Schwartz, Old Westbury, N.Y.

[73] Assignee: R&D Biologicals, Inc., Manhasset, N.Y.

[21] Appl. No.: 384,849

[22] Filed: Feb. 7, 1995

[51] Int. Cl.$^6$ .................................................. A61B 17/68
[52] U.S. Cl. .................. 606/75; 606/77; 606/80; 606/96; 606/104; 606/215
[58] Field of Search .................. 606/75, 72, 60, 606/77, 76, 80, 88, 96, 99, 100, 104, 213, 215, 219; 623/16, 20

[56] References Cited

U.S. PATENT DOCUMENTS

| | | | |
|---|---|---|---|
| 3,208,450 | 9/1965 | Abelson | 606/100 X |
| 3,745,590 | 7/1973 | Stubstad. | |
| 4,055,862 | 11/1977 | Farling. | |
| 4,205,400 | 6/1980 | Shen et al.. | |
| 4,502,161 | 3/1985 | Wall. | |
| 4,627,853 | 12/1986 | Campbell et al.. | |
| 4,808,185 | 2/1989 | Penenberg et al.. | |
| 4,846,835 | 7/1989 | Grande. | |
| 4,873,976 | 10/1989 | Schreiber | 606/75 X |
| 4,880,429 | 11/1989 | Stone. | |
| 4,884,572 | 12/1989 | Bays et al. | 606/75 X |
| 4,895,148 | 1/1990 | Bays et al. | 606/213 |
| 4,963,489 | 10/1990 | Naughton et al.. | |
| 5,059,206 | 10/1991 | Winters | 606/213 |
| 5,067,964 | 11/1991 | Richmond et al.. | |
| 5,123,927 | 6/1992 | Duncan et al.. | |
| 5,176,710 | 1/1993 | Hahn et al.. | |
| 5,180,388 | 1/1993 | DiCarlo | 623/16 |
| 5,197,985 | 3/1993 | Caplan et al.. | |
| 5,246,441 | 9/1993 | Ross et al. | 606/53 |
| 5,261,914 | 11/1993 | Warren | 606/73 |
| 5,263,987 | 11/1993 | Shah. | |
| 5,374,270 | 12/1994 | McGuire et al. | 606/86 |

OTHER PUBLICATIONS

"Surgical Technique For Suretac," Brochure of Acufex Microsurgical (1991), author unknown, 12 pages.

Pagnani, M.J., et al. "Arthroscopic Shoulder Stabilization," Operative Techniques in Sports Medicine, 1, 4 (Cot. 1993) pp. 276–284.

Stuart, M.J., "Treatment of Chronic Chondral Injuries," Sports Medicine and Arthroscopic Review, 2, 50–58 (1994).

Warner, J.J.P., et al., "Arthroscopic Bankart Repair. . .," Operative Techniques in Orthopaedics, 1, 2 (Apr. 1991), pp. 192–198.

"Bioabsorable. . . from Acufex," 1 page Advertisement (1990) Acufex brochure author unknown.

"Bioabsorbable Material Technology: Poly (L–Lactic Acid)" a manufacturer's bulletin available at least as early as 1995, 8 pages.

Vacanti, C.A., et al., "Joint Resurfacing with Cartilage Growth in Situa from Cell–Polymer Structures," The American Journal of Sports Medicine, 22, 4, pp. 485–488 (Jul.–Aug. 1994)

*Primary Examiner*—Guy V. Tucker
*Attorney, Agent, or Firm*—Amster, Rothstein & Ebenstein

[57] ABSTRACT

A method of surgically implanting into a site with cancellous bone a bio-absorbable cartilage repair system including an assembly. The method includes the steps of partially preparing the site to receive the assembly by removing at least a portion of the damaged or destroyed articular cartilage, and then removably fixing the forward tip of a guide wire in the cancellous bone under the removed articular cartilage. The guide wire is then utilized to further prepare the site to receive the assembly by drilling and countersinking the subchondral cancellous bone and to seat the assembly into the drilled and countersunk subchondral cancellous bone until the assembly is flush with the surrounding articular surface. The guide wire is then removed.

21 Claims, 13 Drawing Sheets

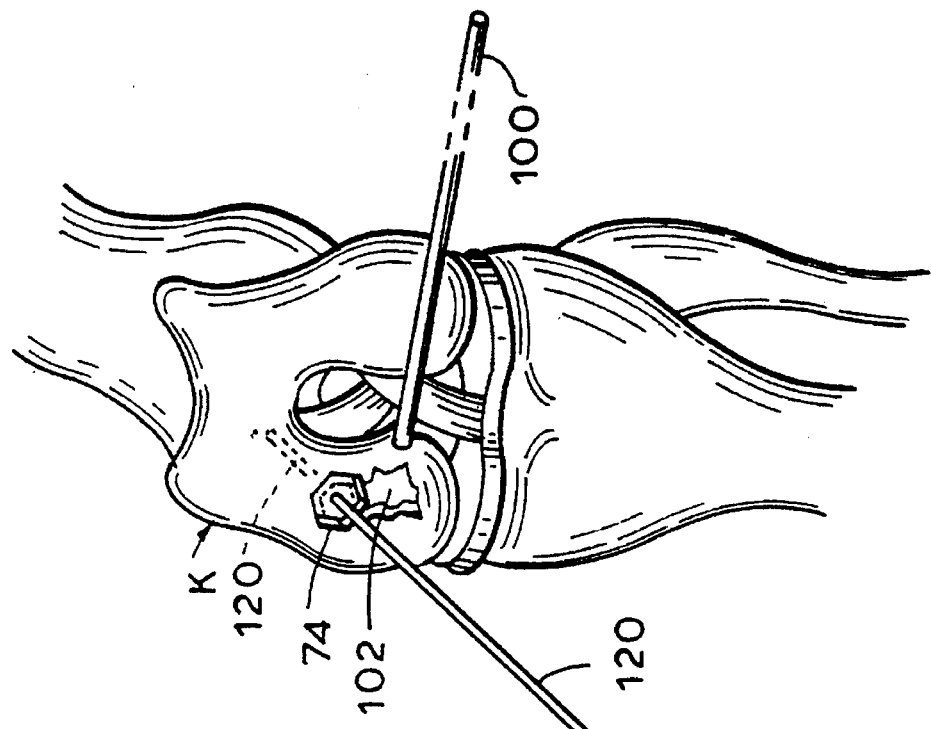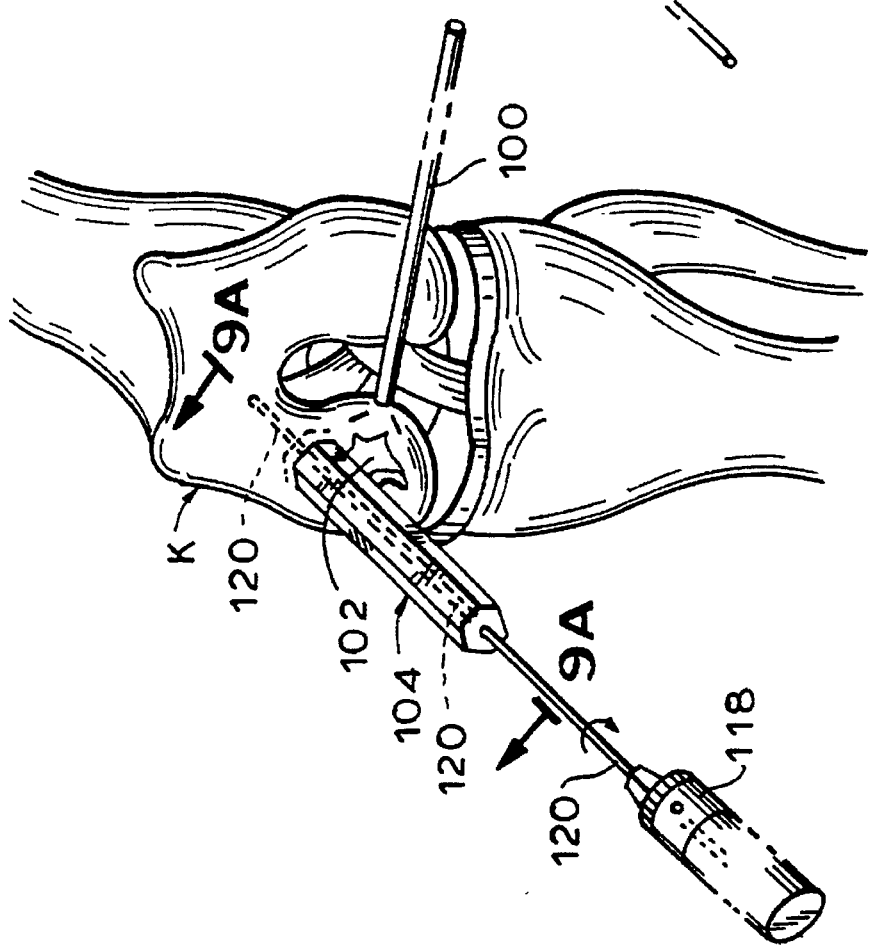

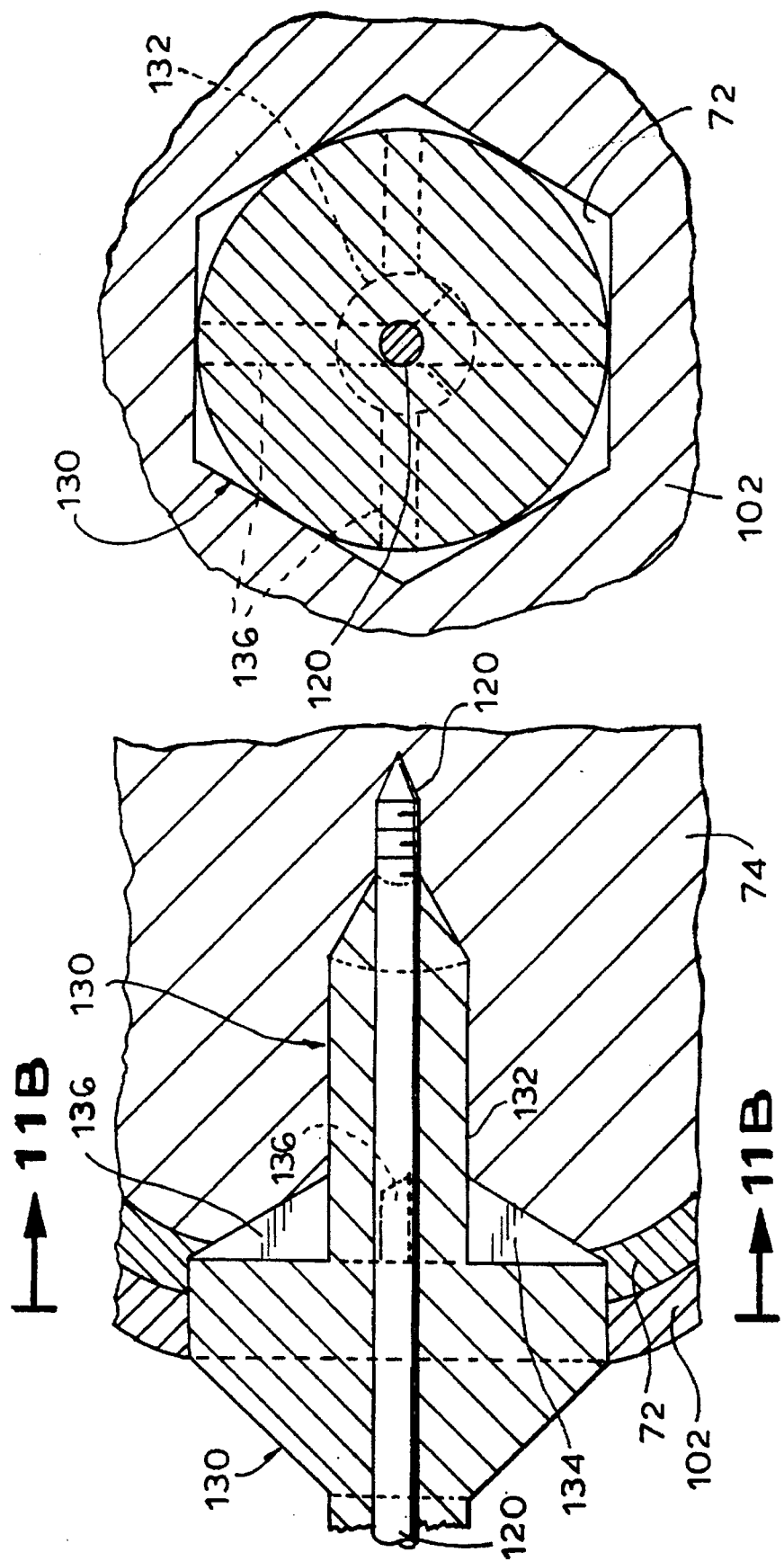

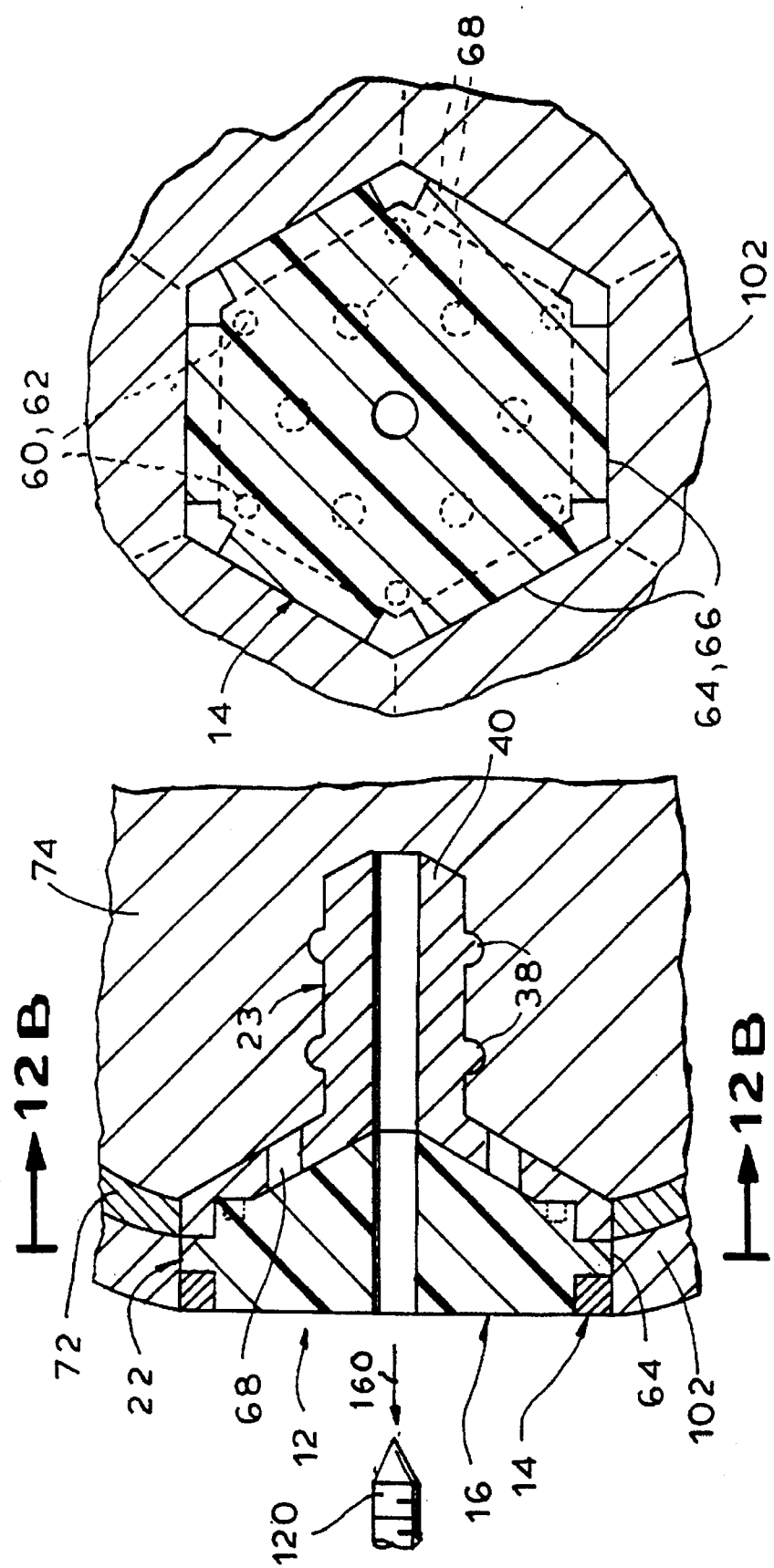

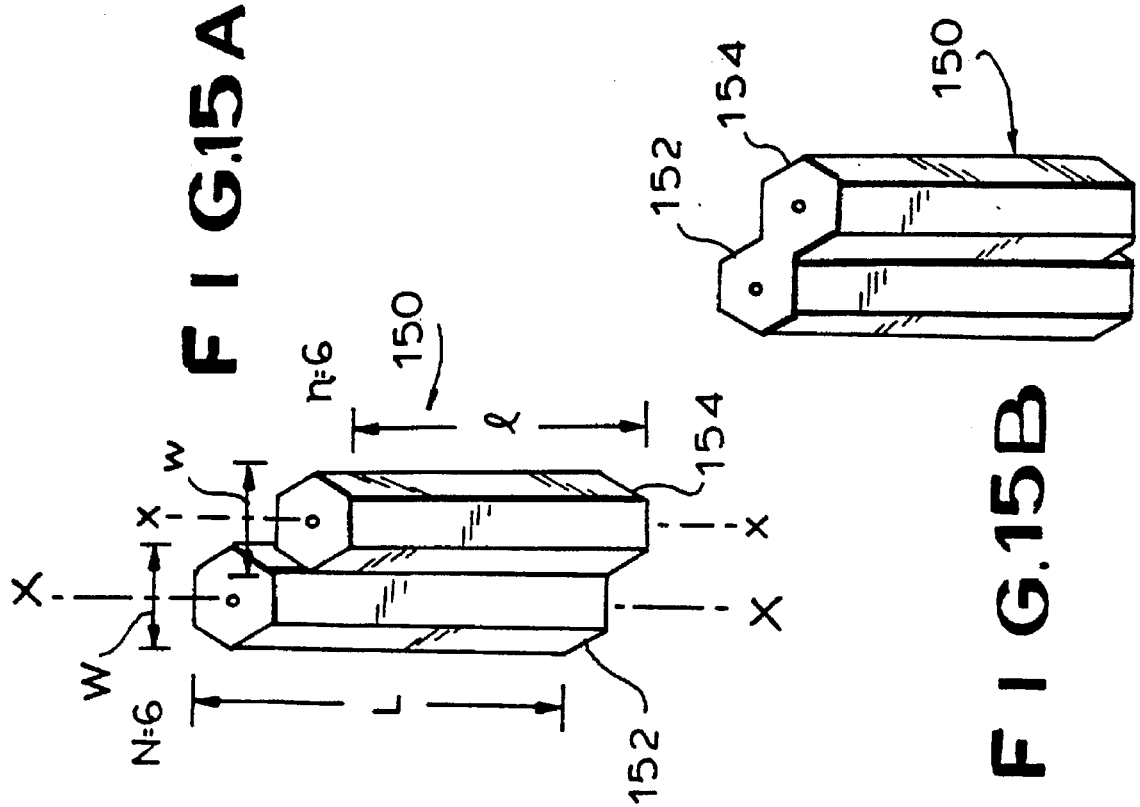
FIG.15A
FIG.15B
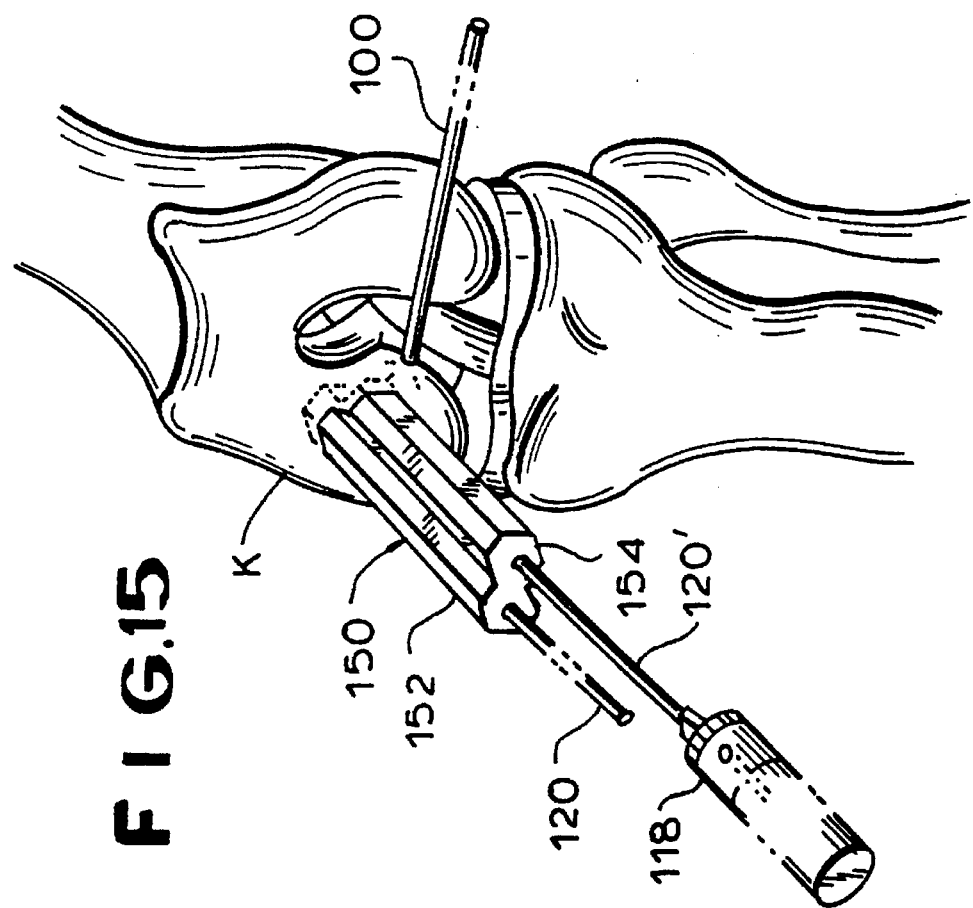
FIG.15

SURGICAL IMPLANTATION OF CARTILAGE REPAIR UNIT

BACKGROUND OF THE INVENTION

This invention relates to a bio-absorbable cartilage repair system for regenerating articular cartilage and, more particularly, a system which allows for vascular invasion and cellular migration between the system and the adjacent healthy area of articular cartilage and cancellous bone, thereby resulting in regeneration of the damaged articular cartilage. More specifically, the present invention relates to a method of surgically implanting such a bio-absorbable cartilage repair system and to apparatus useful therein.

Articular cartilage on the surface of bones in joints, most particularly the knee and hip joints, is susceptible to deterioration caused by injury or disease. This deterioration of cartilage leads to pain and eventually loss of joint movement and severe pain. As a result, various methods have been developed to treat and repair damaged or destroyed articular cartilage.

Prosthetic devices are often used to replace damaged or destroyed articular cartilage. For example, U.S. Pat. No. 4,627,853 discloses prosthesis which are used for articular cartilage replacement. The prosthesis are prepared by demineralization of a bone segment, the demineralized bone segment serving as a replacement for articular cartilage.

U.S. Pat. No. 4,880,429 discloses a prosthetic meniscus which is implanted in the knee. The prosthetic meniscus acts as a scaffold for regrowth of native meniscal tissue, and comprises collagen fibers interspersed with glycoaminoglycan molecules.

U.S. Pat. No. 5,176,710 discloses a prosthesis for replacing bone material on the articulating surface of a joint. The prosthesis has a specific modulus of elasticity so as to confer stiffness to the prosthesis, and contains concave shapes which are suitable for biologic ingrowth.

U.S. Pat. No. 4,502,161 discloses a prosthetic meniscus which replaces the natural meniscus between the articular surfaces of the bones and the joints, and comprises an insert and extension for attachment to the bone and a reinforcing fabric or mesh embedded therein.

U.S. Pat. No. 3,745,590 discloses a prosthesis for the repair or replacement of joints, which prosthesis comprises a body portion, including a stem and ligamentous elements, and allows for tissue ingrowth.

U.S. Pat. No. 5,123,927 discloses a knee prosthesis comprising bone cement containing an antibiotic.

Although there are several prosthetic devices which can be used in the replacement of damaged or destroyed articular cartilage, prosthetic devices have several disadvantages. For example, cements which are used to attach prosthetic devices to bones may loosen and eventually fail. In addition, fragmented cement can move into the joints and associated lymph tissue and cause inflammation and further damage. Further, cements result in the formation of fibrous tissue between the bone and the prosthesis. Another major disadvantage associated with the use of prosthesis is that the prosthetic device may be larger than the damaged cartilage that needs to be replaced, thereby requiring removal of portions of healthy bone and/or cartilage in order to accommodate the prosthetic device. Hence, the need remains for a system for repairing and regenerating articular cartilage which avoids the problems associated with prosthetic devices.

Another means used to treat damaged articular cartilage is the placement of repair pieces onto the bone, which repair pieces substitute for cut-out pieces of cartilage. For example, U.S. Pat. No. 5,067,964 discloses an articular cartilage repair piece which comprises a layer of non-woven, felted fibrous material which is limp and readily conformable to flat and curved surfaces. The articular cartilage repair piece is attached to the bone, for example, by bio-absorbable screws or pins or like temporary fixation techniques. Fibrous tissue ingrowth eventually surrounds the repair piece, thereby causing the repair piece to be permanently attached to the bone. Although U.S. Pat. No. 5,067,964 discloses an alternative method for repairing damaged articular cartilage, it does not disclose any means or method of regenerating damaged or destroyed articular cartilage.

Quite recently, a system for regenerating damaged or destroyed articular cartilage, wherein the regenerated articular cartilage is functionally similar to non-damaged articular cartilage, has been developed. Unfortunately, the method of surgically implanting the system assembly using the conventional tools available to the surgeon is both time consuming and laborious. In addition, where the damaged articular cartilage is of sufficient size to require the surgical implantation of a plurality of the system assemblies rather than just one, the several assemblies should be placed in appropriate juxtaposition relative to one another and to the periphery of the undamaged articular cartilage surrounding the injury. It can be difficult, especially for the inexperienced surgeon, to rapidly and accurately place the several assemblies in appropriate relative locations.

Accordingly, an object of the present invention is to provide a method of surgically implanting a system for regenerating articular cartilage.

Another object is to provide such a method which is relatively fast and easy to perform, even for a surgeon with limited experience in this method.

A further object is to provide in one embodiment such a method involving the placement of a plurality of repair assemblies which utilizes apparatus for determining the placement of one repaired assembly relative to another.

It is another object of the present invention to provide such a method which facilitates a three dimensional approximation of the original surface of the articular cartilage.

SUMMARY OF THE INVENTION

It has now been found that the above and related objects of the present invention are obtained by a method of surgically implanting into a site with cancellous bone a bio-absorbable cartilage repair system including an assembly. The method comprises the steps of partially preparing the site to receive the assembly by removing at least a portion of the damaged or destroyed articular cartilage. Then the forward tip of a guide wire is removably fixed in the cancellous bone under the removed articular cartilage. Utilizing the guide wire, the site is further prepared to receive the assembly by drilling and countersinking the subchondral cancellous bone. Again utilizing the guide wire, the assembly is seated into the drilled and countersunk subchondral cancellous bone until the assembly is flush with the surrounding articular surface. Finally, the guide wire is removed.

In a preferred embodiment, the assembly is adapted to regenerate damaged or destroyed articular cartilage on the surface of a bone by establishing a chondrogenic growth-supporting matrix between an area of damaged or destroyed articular cartilage that has been removed and an adjacent healthy area of articular cartilage and cancellous bone. The assembly includes a bio-absorbable polygonal delivery unit configured and dimensioned to be mounted in both the removed area and the adjacent healthy area of bone, and a porous bio-absorbable insert supported by and in the delivery unit and establishing communication between the removed area and the adjacent healthy area for a chondrogenic growth-supporting matrix.

In the preferred embodiment, the site is partially prepared using a cannulated punch, preferably a polygonal one. The guide wire is inserted through the cannula of the punch after removal of a portion of the damaged or destroyed articular cartilage. A cannulated drill/countersink is passed over the guide wire prior to drilling and countersinking, and the assembly is passed over the guide wire prior to seating.

Preferably the method includes the preliminary step of inserting an arthroscope adjacent the area of damaged or destroyed articular cartilage to enable viewing of the area. The punch is impacted with a mallet until the punch reaches a depth of about 3–4 mm into the articular cartilage and subchondral cancellous bone. The guide wire has a self-tapping threaded forward tip and is rotated by a power drill. A cannulated inserter and then a cannulated impactor are passed over the guide wire after the assembly and then the impactor is used to drive the inserter by itself along the guide wire and against the assembly to seat the assembly in the drilled and countersunk subchondral cancellous bone, followed by removing the inserter and impactor from the guide wire.

The present invention further encompasses a method of surgically implanting into a site with cancellous bone a bio-absorbable cartilage repair system including at least first and second assemblies. The method comprises the steps of proving a spacer for use in spacing apart two guide wires during surgical implantation of the second guide wire a fixed distance from the implanted first guide wire. The site is partially prepared to receive the first assembly by removing at least a portion of the damaged or destroyed articular cartilage. The forward tip of a first guide wire is removably fixed in the cancellous bone under the removed articular cartilage. The spacer and the first guide wire are utilized to removably fix the forward tip of the second wire guide in the cancellous bone a fixed distance from the first guide wire. The second guide wire is then utilized to partially prepare the site to receive the second assembly by removing another portion of the damaged or destroyed articular cartilage. The first and second guide wires are utilized to further prepare the site to receive the assembly by drilling and countersinking the subchondral cancellous bone. The first and second guide wires are then utilized to seat the first and second assemblies, respectively, into the drilled and countersunk subchondral cancellous bone until the assemblies are flush with the surrounding articular surface. Finally, the guide wires are removed.

In a preferred embodiment, the spacer includes a first cannulated polygonal member having an axis X, N sides, a maximum width W and a length L, and a second cannulated polygonal member having an axis x, n sides, a maximum width w, and a length l, where N and W are at least equal to (or exceed) n and w, L exceeds l, and axes X and x are substantially parallel. One side of the first cannulated member and one side of the second cannulated member are rigidly joined. One end of the first cannulated member and one end of the second cannulated member are disposed in the same plane, and the opposite end of the first cannulated member and the opposite end of the second cannulated member are disposed in spaced apart parallel planes. The method including the steps of passing the first cannulated member of the spacer over the first guide wire with the second cannulated member of the spacer disposed over another portion of the damaged or destroyed articular cartilage area, inserting a second guide wire through the cannula of the second cannulated member of the spacer and then removably fixing the forward tip thereof in the cancellous bone, and removing the spacer from both guide wires.

The present invention further encompasses the spacer for use in spacing apart two guide wires during surgical implantation of the second guide wire a fixed distance from the implanted first guide wire, as described above.

BRIEF DESCRIPTION OF THE DRAWING

The above brief description, as well as further objects, features and advantages of the present invention, will be more fully understood by reference to the following detailed description of the presently preferred, albeit illustrative, embodiments of the present invention when taken in conjunction with the accompanying drawings wherein:

FIG. 9 is a view similar to FIG. 8, but with a guide wire being inserted through the punch;

FIG. 10 is a view similar to FIG. 9 but after removal of the punch, leaving there behind the guide wire;

FIG. 11A is a sectional view thereof taken along the line 11A—11A of FIG. 11;

FIG. 11B is a sectional view thereof taken along the line 11B—11B of FIG. 11A;

FIG. 12A is a sectional view thereof taken along the line 12A—12A of FIG. 12;

FIG. 12B is a sectional view thereof taken along the line 12B—12B of FIG. 12A;

FIG. 15 is a view similar to FIG. 9 but showing the seating of a second guide wire using a spacer according to the present invention;

FIGS. 15A and 15B are isometric views of the spacer from the distal and proximal ends, respectively.

DETAILED DESCRIPTION OF THE PREFERRED EMBODIMENTS

Figure 1:
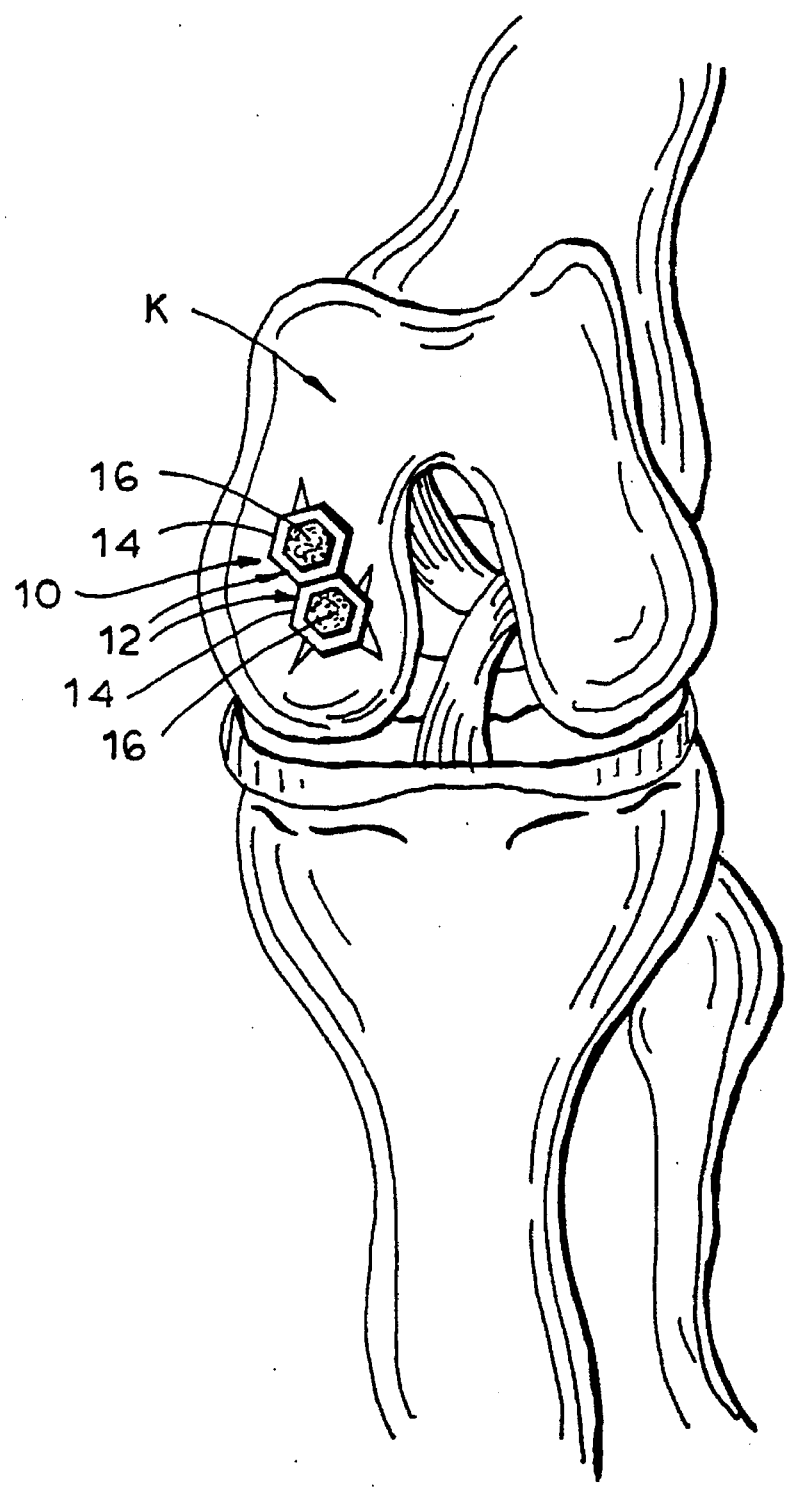
FIG. 1 is a fragmentary schematic view of a knee having therein a pair of assemblies of the cartilage repair system surgically implanted by the method of the present invention.

Referring now to the drawing, and in particular to FIG. 1 thereof, therein illustrated is a cartilage repair system useful in the method of the present invention, generally designated by the reference numeral 10. More particularly, the cartilage repair system 10 illustrated in FIG. 1 is comprised of a plurality of assemblies generally designated 12 (two being illustrated, but it being understood that the requisite number is determined by the extent of the damaged area). Each assembly 12 is in turn comprised of a bio-absorbable delivery unit 14 and a porous bio-absorbable insert 16. The delivery unit 14 is configured and dimensioned to be mounted in both the area from which damaged or destroyed articular cartilage has been removed and the adjacent healthy cancellous bone area of the bone. The porous insert 16 is supported by and in the delivery unit 1& and establishes communication between the removed area (that is, the area from which the damaged or destroyed articular cartilage has been removed) and the adjacent healthy area for a chondrogenic growth-supporting matrix, thereby promoting vascular invasion and cellular migration to achieve articular cartilage regeneration.

Figure 6:
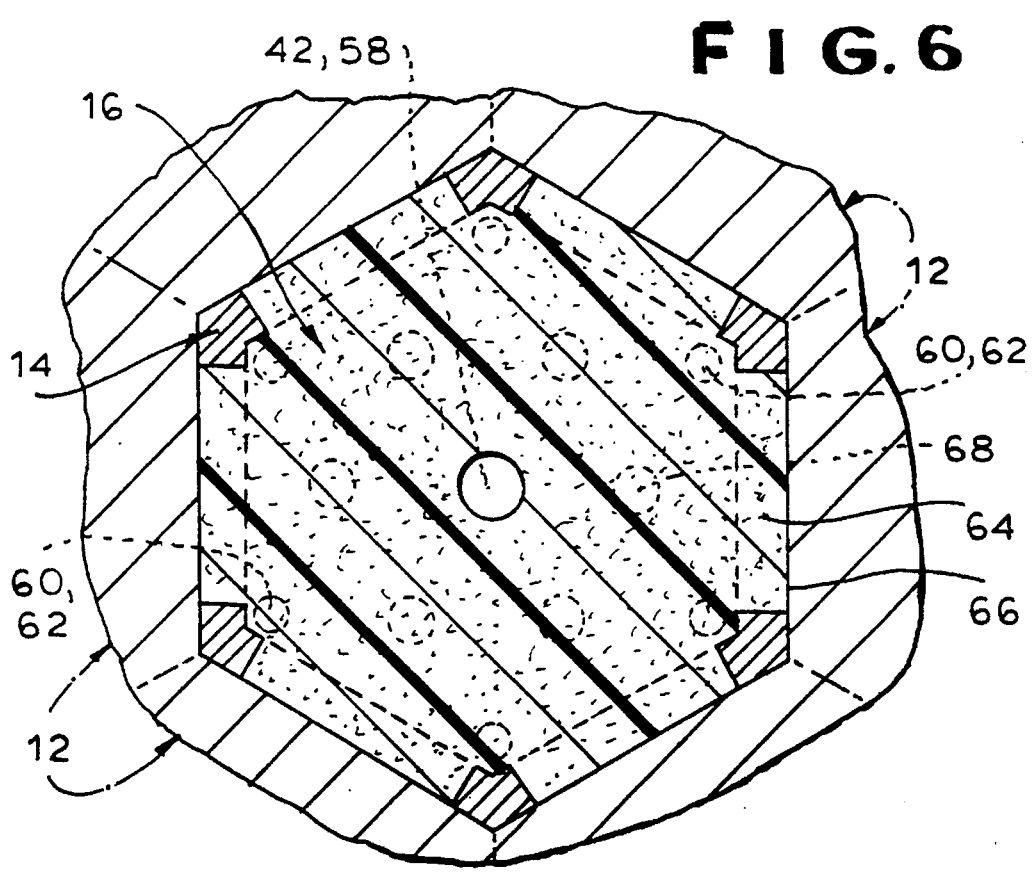
FIG. 6 is a sectional view thereof taken along line 6—6 of FIG. 5, with potential adjacent assemblies being fragmentarily illustrated in phantom line.

While the system 10 is illustrated in FIG. 1 as being used to regenerate damaged or destroyed articular cartilage on the femoral knee joint surface K, those skilled in the medical arts will readily appreciate that the system 10 is equally useful in other articular joints such as the shoulder, hip, and the like. The extent of the damaged or destroyed articular cartilage on the surface of the bone will determine whether the system 10 employs a single assembly 12 or a plurality of assemblies 12. The illustrated assemblies 12 (and in particular the delivery units 14 thereof) are polygonal in plan and interfitting—that is, disposed such that they preferably can be mounted in contiguous abutting contact in a side-to-side relationship. The polygonal nature of the periphery of the assemblies permits interfitting of the assemblies 12 (as generally illustrated in FIG. 6) and is thus preferred where a plurality of the assemblies 12 are to be used to completely cover a designated area of the bone. However, where only a single assembly 12 will be used, other configurations, such as a circular configuration, may be preferred.

While theoretically it might be possible to create in a single manufacturing operation a unitary, one-piece, integral assembly 12 which performs the functions of both the delivery unit 14 and the insert 16, two separate and independently formed components are preferably utilized— namely, the delivery unit 14 and the insert 16. As will be discussed below in detail, the insert 16 can be made of a relatively wide variety of different materials and may even include a repair factor (such as a growth factor or an attachment factor) releasably disposed therein to assist in establishing the chondrogenic growth-supporting matrix. Accordingly, the two-component nature of the assembly 12 enables the insert 16 to be selected from a supply of different inserts 16 at the time of surgery so as to meet the particular needs of the patient at the time with regard to both the basic composition of the insert 16 and any repair factor composition therein. Again, because of the differing natures of the insert 16 (and any repair factors therein) and its delivery unit 14, it may be necessary for particular types of inserts 16 to be stored before use in different environments from the delivery units 14—for example, in order to provide appropriate preservation of the repair factor. Finally, the delivery unit 14 and insert 16 of an assembly 12 must have different functional characteristics which would be difficult to achieve through known manufacturing techniques in an integral, one-piece, unitary element. Thus, as will be discussed below, the delivery unit 14 must have sufficient strength and integrity to enable it to be tamped into the bone without significant bending or deforming, while the insert 16 is preferably a flexible and resilient porous material in the form of a matrix to enable it to be interconnected with the delivery unit 14 and thereby provide a chondrogenic growth-supporting matrix positioned by the delivery unit 14.

Figure 2:
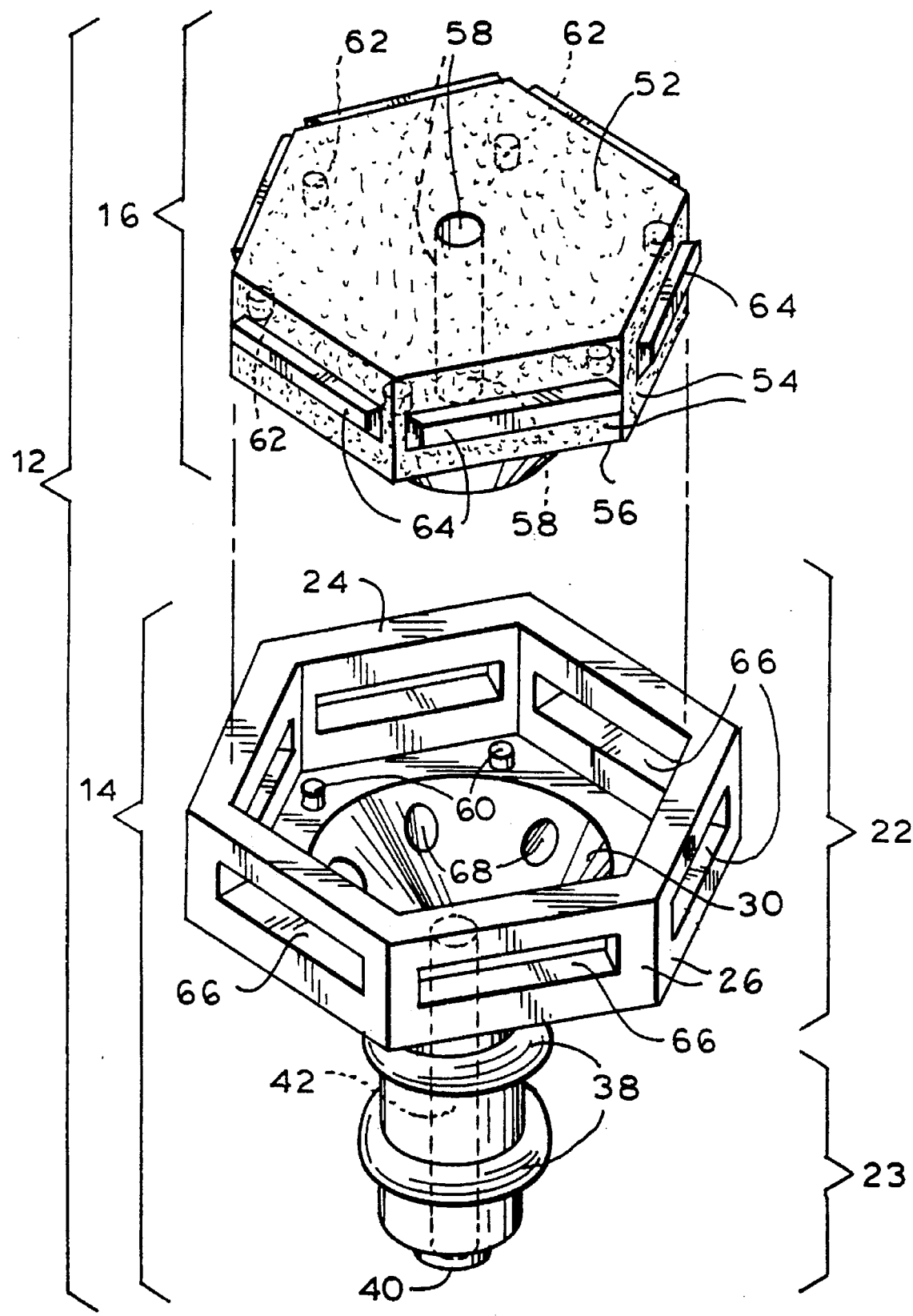
FIG. 2 is an exploded isometric view of one assembly of the cartilage repair system.
Figure 5:
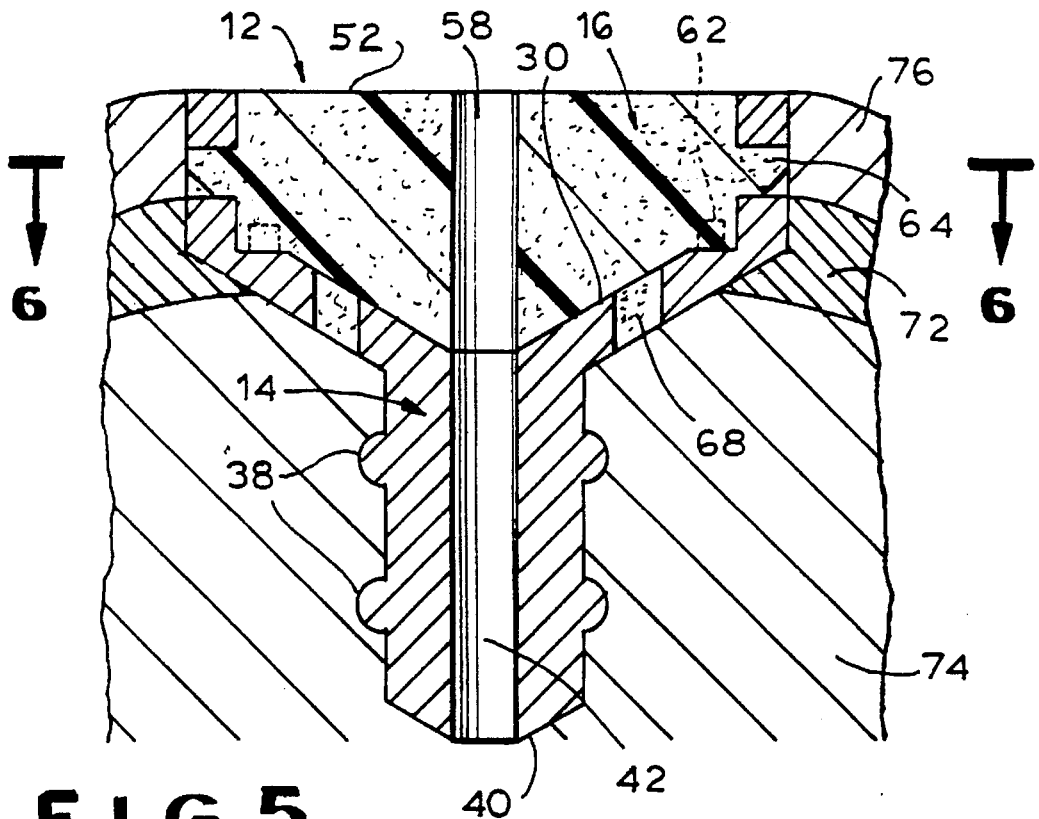
FIG. 5 is a sectional view thereof taken along line 5—5 of FIG. 3 and fragmentarily shows the cartilage repair system inserted into a bone.

Referring specifically to FIGS. 2 and 5, delivery unit 14 is comprised of an upper cup-like support frame 22 and a lower T-like elongate member 23. The support frame 22 has an upper rim 24 defining an open top, side walls 26 and a bottom portion 30. The elongate member 23 (which is preferably cylindrical) extends downwardly from the bottom portion 30 (which is preferably concave) and has radially extending ribs 38, a blunt bevelled bottom 40 and a bore 42 (preferably about 1.5 mm in diameter) extending axially there through. The disc or waferlike insert 16 has a top surface 52, side walls 54, a bottom surface 56 and a bore 58 (preferably about 1.5 mm in diameter) extending axially there through and after insertion into delivery unit 14 coaxial with bore 42 thereof.

The support frame 22 of the delivery unit 14 receives the insert 16 therein, with the side walls 26 of the support frame 22 receiving there within the side walls 54 of the insert 50. The bottom surface 56 of the insert 16 and the bottom portion 30 of the support frame 22 are correspondingly shaped, preferably with the bottom surface of the insert 16 defining a protrusion and the upper surface of the bottom portion 30 defining a protrusion-receiving cavity, so that the two bores 42, 58 are automatically and accurately coaxially disposed after the insertion process. In other words, when the insert 16 is secured in the supporting frame 22, the bore 42 through the elongate member 23 and the bore 58 through the insert 16 are in vertically aligned contiguous relationship.

As will readily be appreciated by those skilled in the implant arts, if vascular invasion and cellular migration is to be effected between the healthy cancellous bone area and the area of removed damaged cartilage via the insert 16, means must be provided to preclude relative rotation of the delivery unit 14 and the insert 16. This may be accomplished in a number of different ways.

Figure 3:
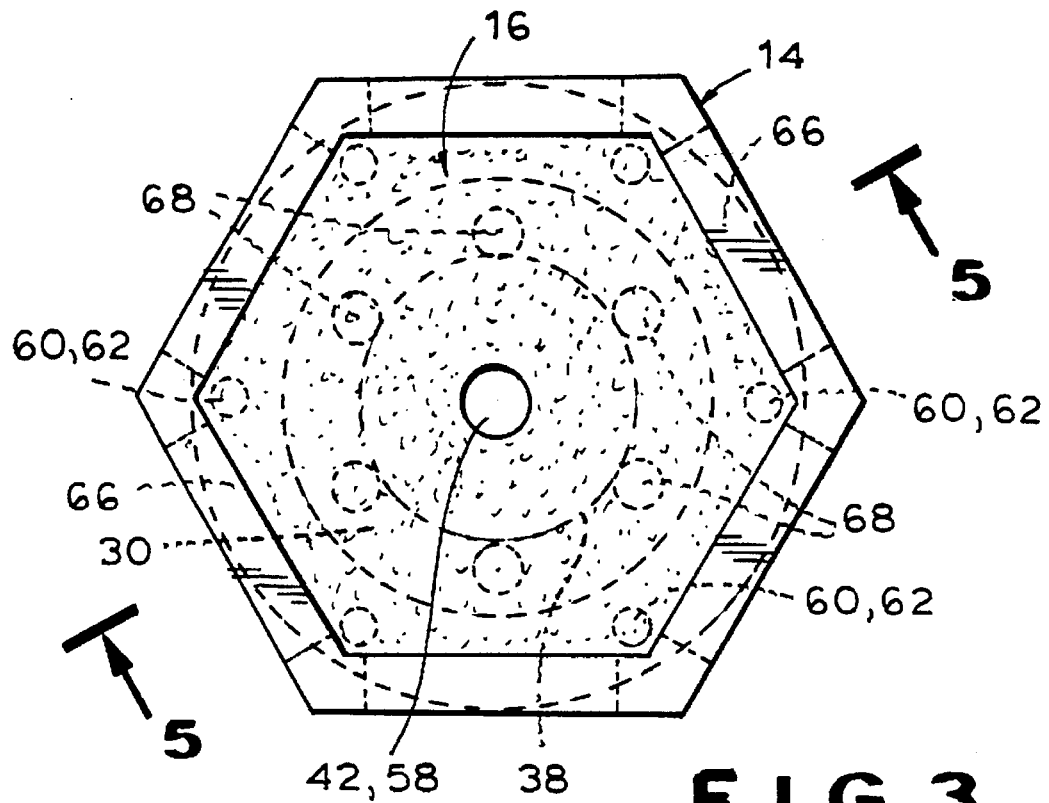
FIG. 3 is a top plan view thereof.

First, as best seen in FIGS. 2–3 and 6, the external periphery of the insert 16 and the internal periphery of the support frame 22 may be polygonal or irregular (that is, non-circular) and sized to abut one another so that they are locked together for rotation only as a unit. For example, as illustrated, the hexagonal outer periphery of insert 16 snugly fits within hexagonal inner periphery of support frame 22 to preclude relative rotation.

Second, the upper surface of the concave bottom portion 30 of the support frame 22 may define upwardly extending bosses 60 adjacent the side walls 26, while the lower surface of the insert 16 may define upwardly extending recesses 62 configured and dimensioned to receive the bosses 60, as best seen in FIGS. 3 and 6. When a boss/recess system is employed, the number of bosses 60 and recesses 62, as well as the shape, size and placement thereof, are selected so that, when the insert 16 is within the delivery unit 14, the bosses 60 are snugly received in the recesses 62, such that the insert 16 and delivery unit 14 are precluded from relative rotation as long as the insert 16 is within the support frame 22.

Third, the side walls 54 of the insert 16 may define radially outwardly extending flanges 64 therein or therethrough, and the side walls 26 of the support frame 22 may define windows 66 there through configured and dimensioned to snugly receive the flanges 64 therein or there through. The number of flanges 64 and windows 66, as well as the size, shape and spacing thereof, are selected so that, when the insert 16 is within the support frame 22, relative rotation of the insert 16 and the delivery unit 14 is precluded as long as the flanges 64 snugly extend into (and possibly through) the windows 66. In order to enable the insert 16 with its flanges 64 to be easily inserted into the supporting frame 22 with its windows 66, the insert 16, or at least the flanges 64 thereof, are preferably resiliently flexible. The flanges 64 or windows 66 may also have bevelled edges to facilitate snapping the flanges 64 into the windows 66 during the insertion process.

In the last two alternatives, the height of the bosses 60 and the depth of the recesses 62 or the relative heights of the flanges 64 and windows 66 are selected so that the bottom surface 56 of the insert 16 will rest on the upper surface of the bottom portion 30 of the delivery unit 14. It will be appreciated by those skilled in the mechanical arts that a wide variety of different keying mechanisms well known in the mechanical arts may be used in order to preclude relative rotation of the insert 16 and the delivery unit 14. However, it must be kept in mind that, over time, the bio-absorbable elements—that is, the delivery unit 14 and the insert 16—will be disappearing as the human body hydrolyzes the material from which they are made. Accordingly, the selection of an appropriate keying mechanism to preclude relative rotation of the insert 16 and the delivery unit 14 must be made with this consideration in mind. It will be appreciated that while, for the purposes of exposition, a variety of different keying mechanisms have been illustrated in a single embodiment, in fact a single keying mechanism may suffice for a particular embodiment, although a plurality of such mechanisms may also be used.

In order to enable the insert 16 to function as a chondrogenic growth-supporting matrix, it must have access to vascular invasion and cellular migration to regenerate the articular cartilage defect. Such access is provided on the internal periphery of the insert 16 by the bore 58. On the external periphery of the insert 16, the windows 66 on the supporting frame 22 provide direct contact to the adjacent healthy articular cartilage or to the adjacent repair assemblies. These windows 66 allow cellular migration to occur to the insert. The entire top surface 52 of the insert 16 is exposed to the articular environment of the affected joint, and a substantial portion of the bottom surface 56 of the insert 16 is exposed to the cancellous bone through channels 68, which extend axially through the bottom 30 of support frame 22. Providing communication between the area of removed damaged articular cartilage and the healthy cancellous or trabecular bone, the number of the channels 68, as well as the size, shape and placement thereof, is selected to provide a desirable level of communication without unduly deleteriously affecting the strength of the delivery unit 14. The axially disposed channels 68 are, of course, disposed radially outwardly of the elongate member 23 so that the channels 68 do not have to extend axially there through.

The delivery unit 14 is hard and preferably does not bend or deform under expected pressures. It is preferably integrally molded. It is critical that the delivery unit 14 be made of a bio-absorbable material such as those well known in the implant art. For example, it is preferably made of polyglycolic acid, polylactic acid or combinations thereof (e.g., co-polymers and mixtures thereof).

Several delivery units 14 can be placed contiguously in an area of removed damaged articular cartilage such that a large portion of the removed area will be filled with the assemblies 12. In this case, the delivery units 14 are preferably regular polygons and interfitting in an abutting and contiguous relation. A circular delivery unit may be used where only one delivery unit is employed or where only partial coverage of the removed area is desired.

The insert 16 is made substantially of porous material in the form of a matrix or sponge, preferably defining at least 95% voids by volume, so that it can serve as a biological scaffold for an invasion of cells to regenerate the articular cartilage. It typically has the felt-like feel of a non-woven fabric. The insert 16 may be manually bendable or flexible when it is necessary to push, press or snap the same into the delivery unit 14. It is critical that the insert 16 consists substantially (typically at least 99% by weight) of a bio-absorbable material selected from the group consisting of hyaluronic acid (e.g. as a fiber matrix), polyglycolic acid (e.g., as fiber matrix), collagen, including type I collagen (e.g., as a sponge matrix), polylactic acid (e.g. as a fiber matrix), fibrin clot (which can be filled and molded into the delivery unit), collagen gel (which can be overlayed into a polyglycolic acid matrix), isolated periosteal cells, polydioxane, polyester, alginate or combinations thereof. The polylactic acid, and to a lesser degree the hyaluronic acid, polyglycolic acid, and alginate, contribute to the hardness and longevity (i.e., life in situ after implantation) of the insert 16. The insert may be annealed (i.e., heat-treated or cooked) to modify its crystallinity and thus its hardness and longevity. The isolated periosteal cells may be cultured in the insert material or overlaid at the time of surgery into the insert material. Other cell types, such as mesenchymal stem cells or chondrocytes, may also be added to the insert material.

In addition, preferably the insert 16 contains within the matrix "repair factors" such as growth factors and/or attachment factors well known in the medical arts. For example, the insert 16 can contain, as growth factors, fibroblast growth factor (acidic or basic), transforming growth factor-beta (1, 2, 3 or one of the members of the supergene family of TGF-beta, such as bone morphogenic protein; BMP), insulin, insulin-like growth factor 1 & 2, platelet-derived growth factor or combinations thereof. The attachment factors which can be used in the insert include fibronectin, RGD polypeptide and combinations thereof. Typically, the repair factors total less than 1% by weight of the insert, but can range up to 10% depending on the factors' specific activities and release kinetics. The repair factors may be chemically combined with the basic implant composition (e.g., during polymerization thereof) or may be added to an already formed basic implant composition. In the former case, additional repair factor will typically become available as the basic implant composition biodegrades.

Referring now to FIG. 5, after surgical removal of the damaged or destroyed articular cartilage, the elongate member 23 (extending downwardly from the concave bottom portion 30 of the support frame 22) is placed into the cancellous bone 74 through the subchondral bone plate 72 which is below the damaged articular cartilage area. The support frame 22 is supported by the subchondral bone plate 72. The elongate member 23 has a blunt bevelled bottom 40 so that the elongate member 23 can be placed easily into the cancellous bone 74, which is a soft region of the bone, while still creating frictional retention of the elongate member. The bottom 40 of the elongate cylindrical member 23 is blunt so that the bottom 40 does not break when the elongate cylindrical member 23 is placed inside the cancellous bone 74. When the elongate member 23 is placed into the soft cancellous bone 74, the cancellous bone 74 is displaced by, and reforms around, the radially extending ribs 38 of the elongate member 23. In this manner, the elongate member 23, and thereby the entire cartilage repair system 10, is held in place.

When the delivery unit 20 is placed in the bone, the upper rim 24 of the support frame 22 is flush with undamaged articular cartilage 76. The windows 66 and the upper rim 24 of the support frame 22 are not placed inside the bone, but rather remain exposed to the surrounding articular cartilage. The top surface 52 of the polymer insert 50 is exposed to the joint space environment. The top portion of the exterior surface of the side walls 26 of the support frame 22 laterally abuts either the top portion of the exterior surface of the side walls 26 of adjacent support frames 22 (see FIG. 6), or undamaged peripheral articular cartilage 76 when placed adjacent to an area of removed cartilage. The bottom portion of the exterior surface of the side walls 26 of the support frame 22 (i.e., the portions below windows 66) rests on and laterally abuts the subchondral bone plate 72.

When the cartilage repair system is placed in an area of removed damaged articular cartilage, through the subchondral bone plate 72 into the cancellous bone 74, the channels 68 in the bottom portion 30 of the support frame 22 allow for communication between the healthy cancellous bone 74 and the damaged articular cartilage area via a chondrogenic growth-supporting matrix. This permits vascular invasion and cellular migration, which results in regeneration of the articular cartilage. The regenerated articular cartilage is functionally similar to undamaged articular cartilage. The cartilage repair system of the invention is bio-absorbed over time and therefore need not be surgically removed during or after cartilage regeneration. The absorption rate is formula controlled and can range from 6–12 weeks to one year depending on its site-specific application.

As the basic bio-absorbable composition of the insert 16 degrades or hydrolyzes over time, any repair factors contained therein are progressively released into the site, thus further promoting cellular regeneration. Cellular regeneration occurs throughout the insert.

The term "bio-absorbable" is used in the specification and claims hereof to indicate a material which will be degraded or absorbed by the body such that regenerated articular cartilage thereabout is functionally similar to non-damaged articular cartilage.

Referring now to FIGS. 7–13 in sequence, therein illustrated is the method of surgically implanting into a site with cancellous bone a bio-absorbable cartilage repair system 10 including an assembly 12, according to the present invention.

Figure 7:
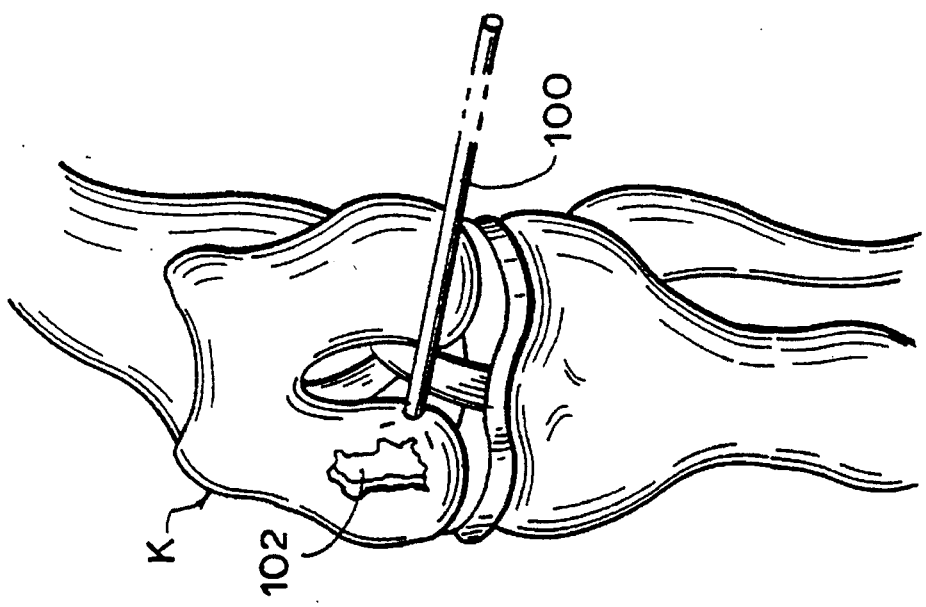
FIG. 7 is a fragmentary schematic view of a knee having damaged or destroyed articular cartilage, with a arthroscope being disposed adjacent thereto according to the method of the present invention.

Referring now to FIG. 7 in particular, a conventional arthroscope 100 is disposed adjacent the femoral condyle to provide the surgeon with a relatively unobstructed view of the injury site 102 (herein illustrated as part of the knee K).

Figure 8:
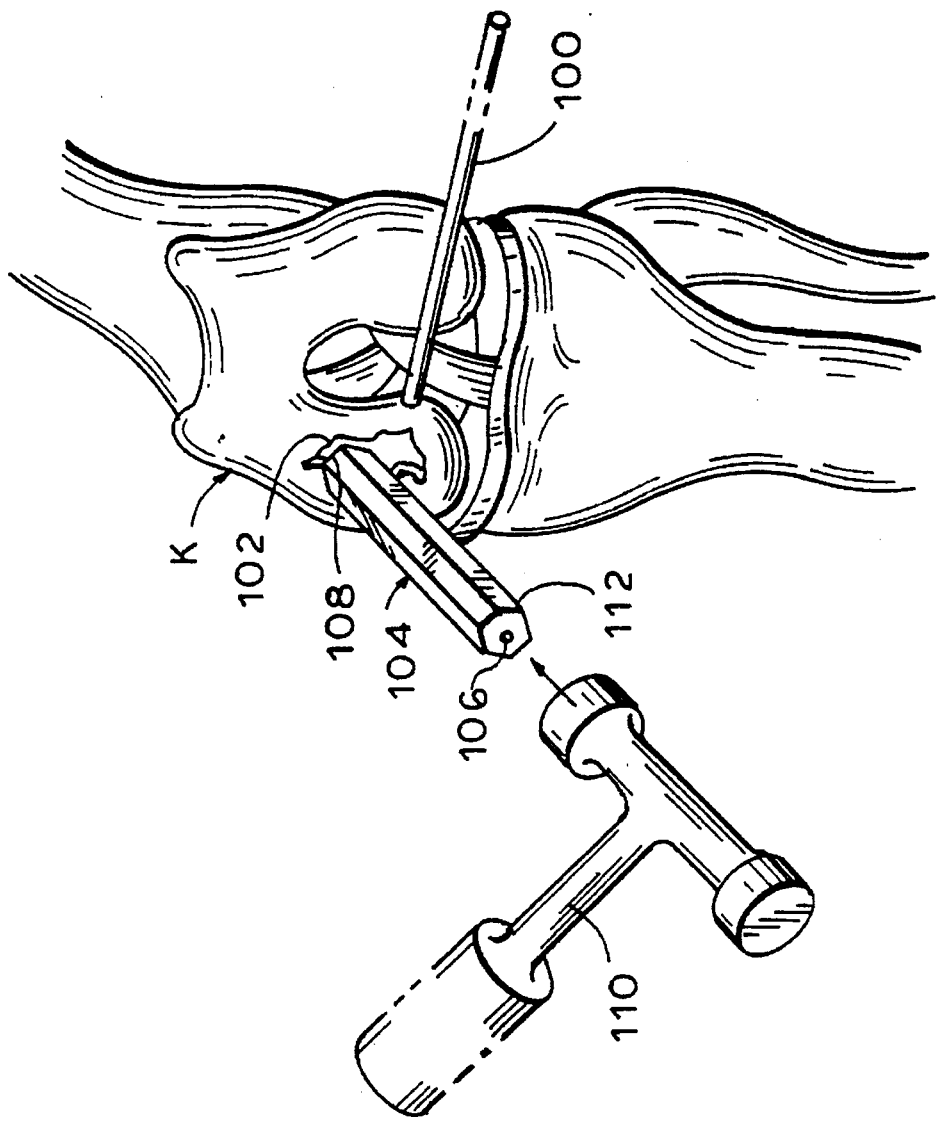
FIG. 8 is a view similar to FIG. 7, but showing a mallet pounding a cannulated punch into the damaged or destroyed articular cartilage to remove the same.
Figure 9B:
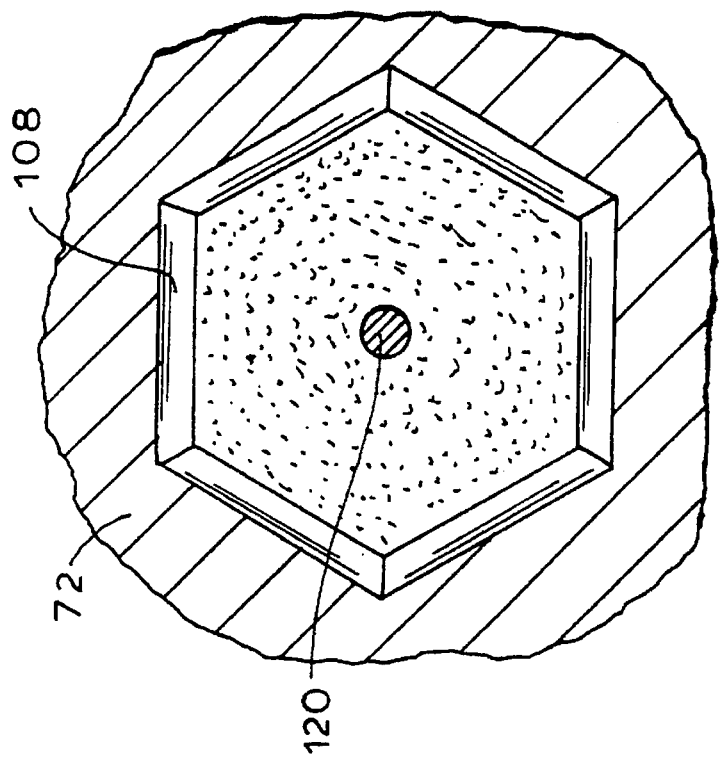
FIG. 9B is a sectional view taken along the line 9B—9B of FIG. 9A.
Figure 9A:
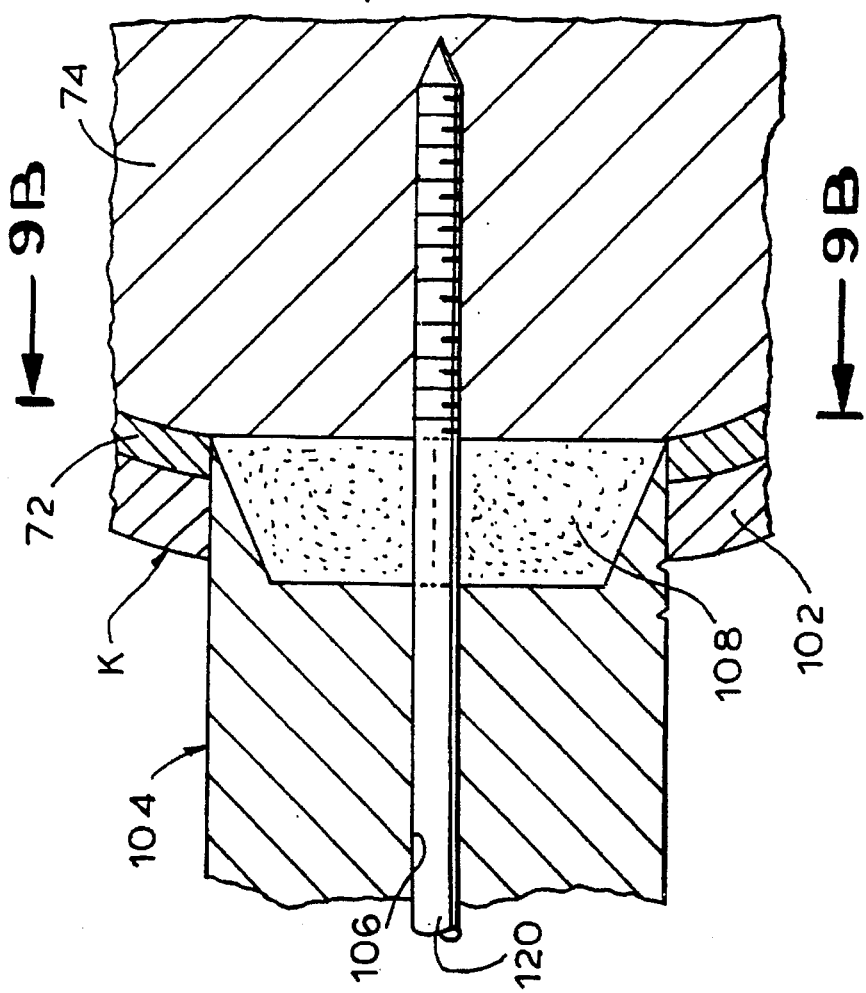
FIG. 9A is a sectional view taken along the line 9A—9A of FIG. 9.

Referring now to FIG. 8 in particular, the site of the injury is partially prepared to receive the assembly 12 by removing at least a portion of the damaged or destroyed articular cartilage. To this end, a cannulated punch 104 (as best illustrated in FIGS. 9A and 9B) is provided. The punch, generally designated 104, defines a cannula 106 of sufficient diameter to accommodate a guide wire passing therethrough and an outer or lateral configuration which preferably matches that of the assembly 10. The distal end 108 of the punch 104 is configured and dimensioned to remove all of the damaged or destroyed articular cartilage where only a single assembly 12 will be deployed, and to remove at least a portion of the damaged or destroyed articular cartilage when a plurality of assemblies 12, 12' will be deployed (as best seen in FIG. 6). The width of the punch distal end 108 is preferably selected to abut against the healthy articular cartilage about the injury site (unless the assembly 12 to be inserted will subsequently be surrounded by other assemblies 12'). Except for the cannula 106 extending therethrough, the distal or cutting end of the punch 104 is of conventional design. The distal punch end 108, when tapped home, removes at least a portion of the aligned damaged or destroyed articular cartilage 102 and the subchondral bone plate 72 intermediate the damaged articular cartilage 102 and the cancellous bone 74 (as best seen in FIG. 9). FIG. 8 shows a conventional surgeon's mallet 110 being used by a surgeon to impact the proximal or near end 112 of punch 104, thereby to drive the punch distal end 108 into the damaged or destroyed articular cartilage 102 and the subchondral bone 72. Preferably the punch 104 is inserted to a depth of about 3–4 millimeters into the articular cartilage and subchondral cancellous bone plate 72 (as measured from the cartilage outer surface).

Referring now to FIGS. 9–9B in particular, A conventional surgeon's power drill 118 or like instrument is used to rotate and drive a guide wire 120 through the punch cannula 106 (through the punched-out segment of damaged or destroyed articular cartilage and the subchondral bone plate 72, yet to be removed) and into the cancellous bone 74. To this end the distal end of the guide wire 120 is preferably threaded and self-tapping. The guide wire 120 is preferably 1.25 millimeter in diameter, and formed of stainless steel, titanium, or another material which, at least over the short period of the implantation operation, is biocompatiable and generally rigid (at least when disposing in a channel such as punch cannula 106).

Referring now to FIG. 10 in particular, as the power drill 118, and then the punch 104 are withdrawn from the guide wire 120, the punch distal end 108 takes therewith the removed portion of the damaged or destroyed articular cartilage 102 and the underlying portion of the subchondral bone plate 72, thereby exposing to view the cancellous bone 74 therebelow. Due to limitations on the size of the cutting recess of the punched distal end 108, it may not be possible to remove in a single step all of the damaged or destroyed articular cartilage 102 and the underlying portion of the subchondral bone plate 72 aligned with the punch 104. In this instance, after the detritus has been removed from the punch distal end 108, the punch 104 may be passed over the guide wire 120 (which enters the cannula 106) and driven home again by the mallet 110, and detritus removed with standard arthroscopic instruments.

Where appropriate the cannulated punch 104 may be configured as a cannulated chisel or like tool for performing the same function.

Figures 11, 12:
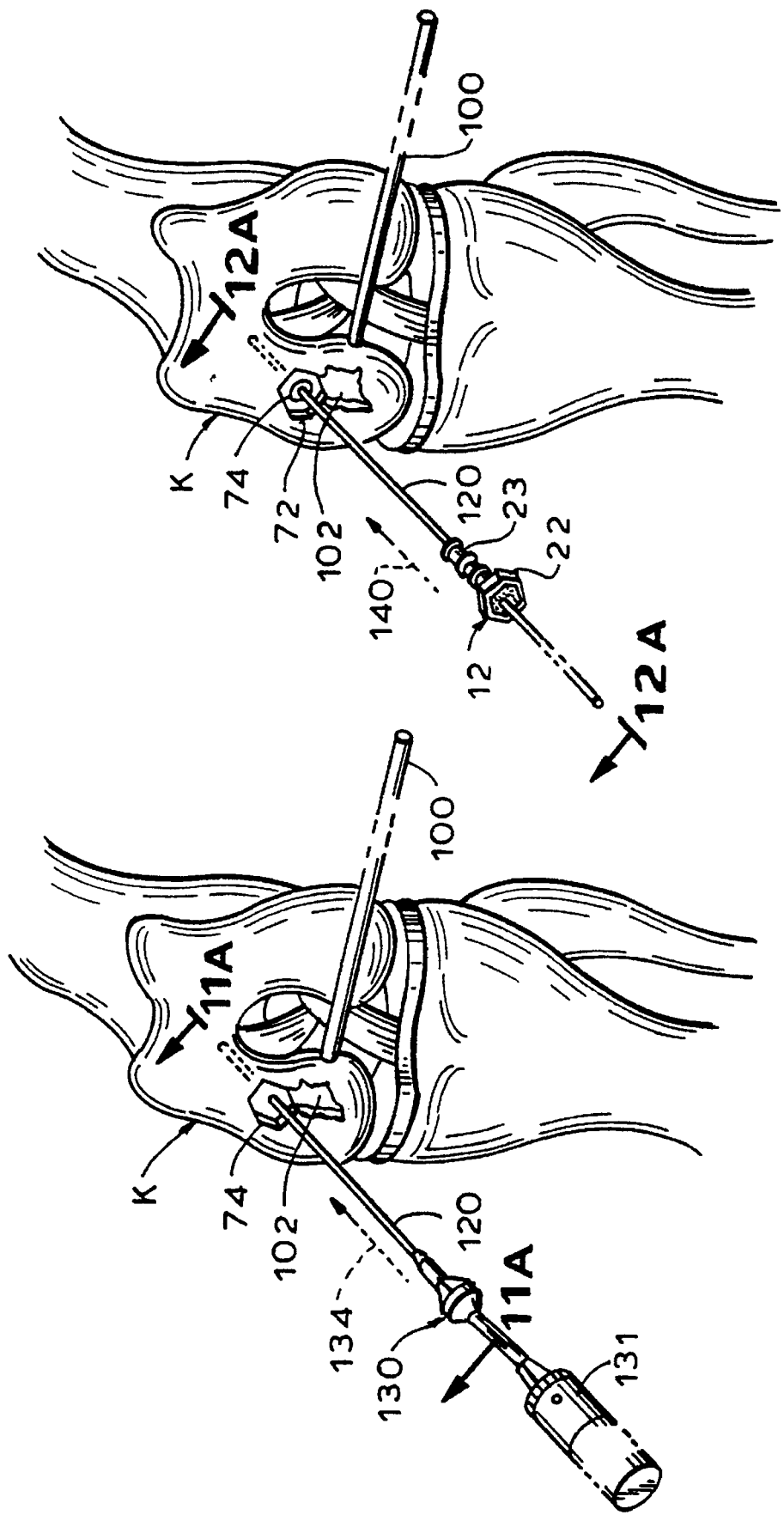
FIG. 11 is a view similar to FIG. 10, but with a cannulated drill/countersink on the guide wire.
FIG. 12 is a view similar to FIG. 11, but with the assembly passing over the guide wire.

Referring now to FIGS. 11–11B in particular, a cannulated drill/countersink, generally designated 130, mounted on a power drill 131 (which may be the same or a different power drill then the power drill 118) is then slid over the proximal end of guide wire 120 and advanced in the direction of arrow 134 to drill and countersink the subchondral bone plate 72.

Figure 4:
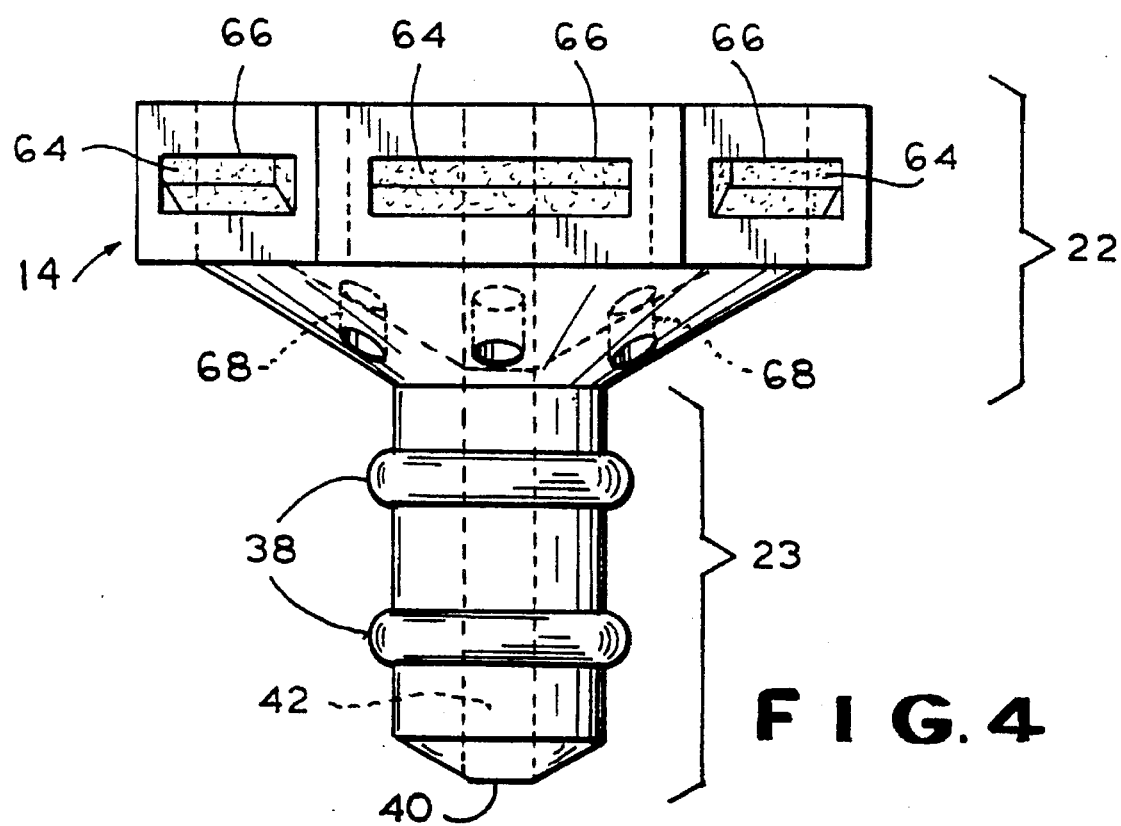
FIG. 4 is a side elevational view thereof.
Figure 11C:
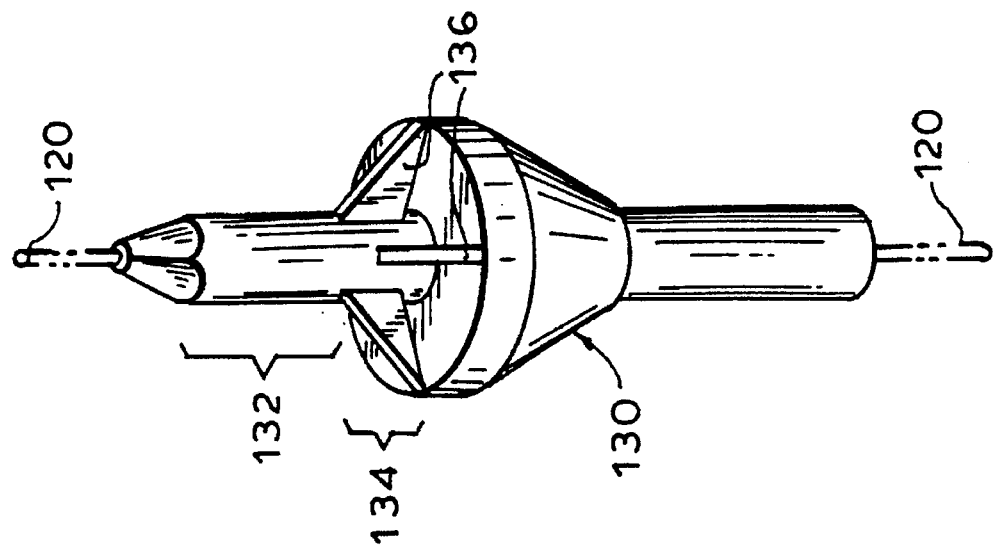
FIG. 11C is an isometric view of the drill/countersink shown in FIG. 11, to a greatly enlarged scale.

Referring now to FIG. 11C in particular, therein illustrated is a drill/countersink 130 according to the present invention. Comparing FIG. 11C and FIG. 4, it will be appreciated that the distal end 132 of the drill/countersink 130 is similar to the elongate member 23. A central portion 134 of the drill/counter sink 130 has ribs 136 at an angle similar to the bottom 30 of the support frame 22 (see FIG. 2). Thus, the forward drill/countersink portion 132 provides an opening in the cancellous bone for the elongate number 23 while the central drill/countersink portion 134 provides a countersink opening for bottom 30 partially in the cancellous bone 74 and partially in the subchondral bone plate 72.

Referring now to FIGS. 12–12B in particular, after removal of the power drill 131 and the drill/countersink 130 from the guide wire 120, the assembly 12 is mounted over the proximal end of the guide wire 120 and advanced forwardly in the direction of arrow 140 into the drilled and countersunk subchondral cancellous bone until the assembly 12 is flush with the surrounding articular surface. Surgeons of substantial experience with implantation of the assembly 12 should choose to use a conventional cannulated mallet (not shown) disposed over the guide wire 120 for seating the assembly 12 in the cancellous bone 74. However, care must be taken to ensure that the mallet does not cause the assembly 12 to impact upon the subchondral bone plate 72 and cancellous bone 74 with sufficient force to damage either the bone or the assembly.

Figure 13:
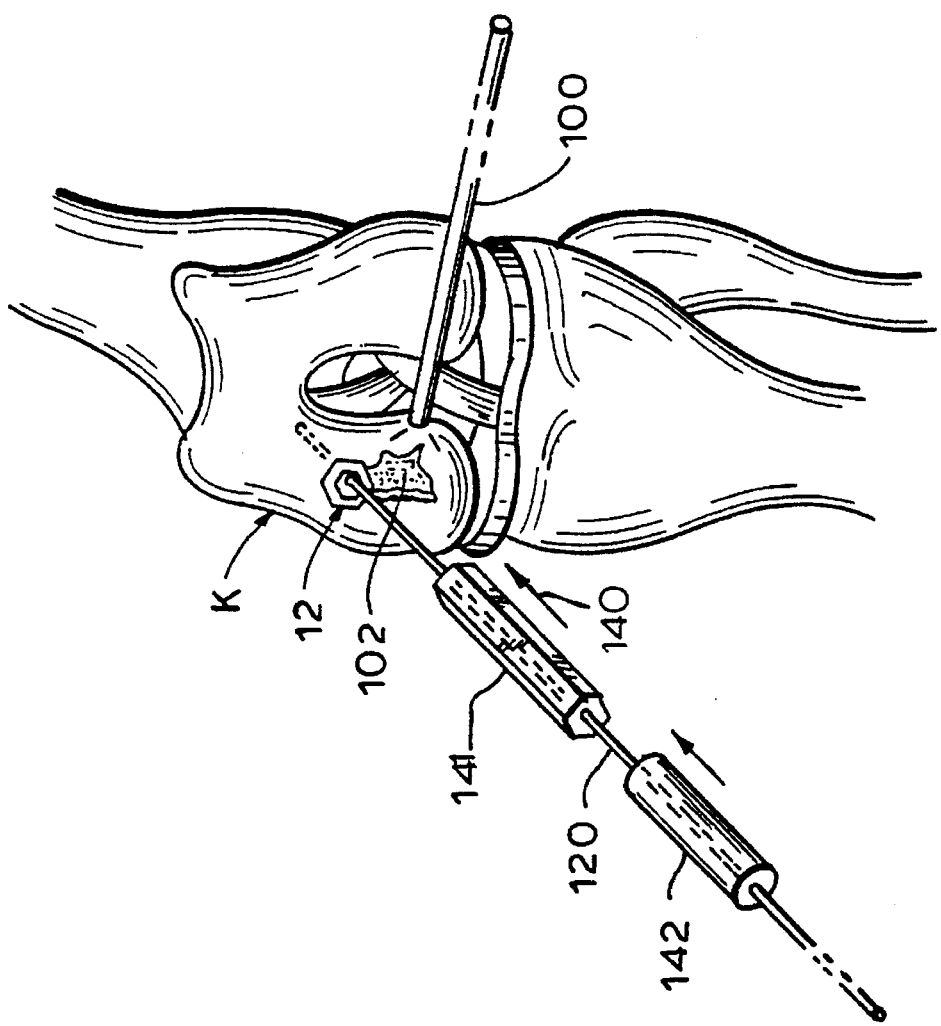
FIG. 13 is a view similar to FIG. 12, but showing the assembly being seated, with a cannulated inserter and a cannulated impactor being shown on the guide wire.

Referring now to FIG. 13 in particular, in order to avoid the possibility of damage from the assembly seating procedure, in a preferred embodiment of the present invention after the assembly 12 is mounted on the guide wire 120 a cannulated assembly inserter 141 and a cannulated impactor or mallet 142 are disposed on the guide wire 120. (The cannulated punch 104 should not be used as the cannulated inserter 141.) The cannulated impactor 142 is a device of known weight selected so that, when the surgeon manually moves it rapidly along the guide wire 120 until it impacts the inserter 141, it imparts a predictable momentum to the inserter 141 such that the assembly 12 is seated in the drilled and countersunk subchondral cancellous bone without damage either to the bone or the assembly. Thereafter the impactor 142 and the inserter 141 are in turn removed from the guide wire 120. Accordingly, even an inexperienced surgeon can rapidly and safely seek the assembly 12 into its previously prepared site.

Figure 14:
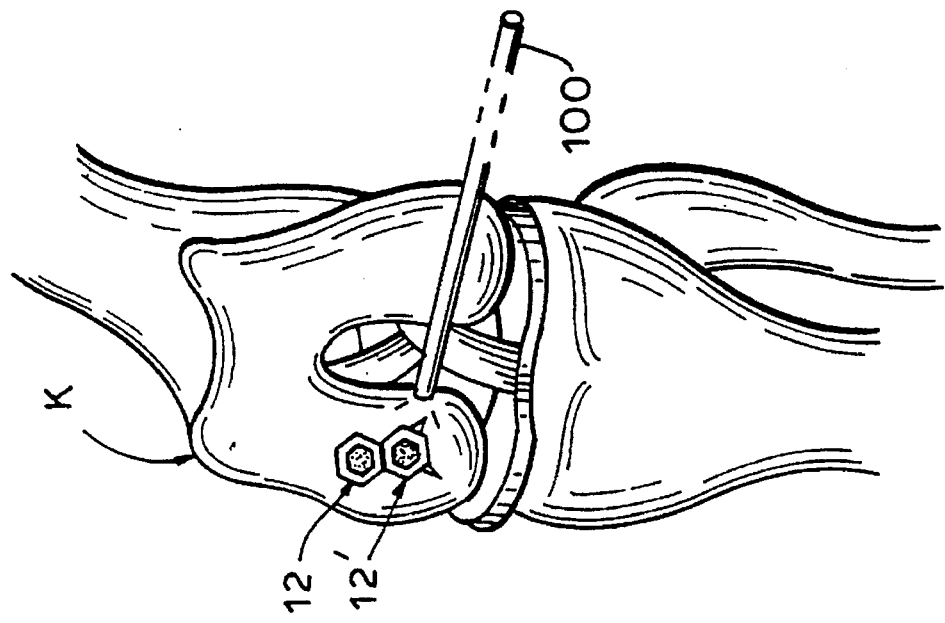
FIG. 14 is a view similar to FIG. 13 wherein, after removal of the inserter and impactor, the procedure has been repeated to implant another assembly adjacent to the first assembly.

Finally, the guide wire 120 is removed either manually or with a power drill. FIG. 12A shows the guide wire 120 being withdrawn in the direction of arrow 160 from the implanted assembly 12.

Where necessary, as illustrated in FIG. 14, additional portions of the destroyed or damaged articular cartilage 102 may be removed and replaced with a second assembly 12', following the procedures outlined above, until substantially all of the damaged or destroyed articular cartilage 102 has been removed and replaced by assemblies 12, 12'. At that point, the arthroscope 100 may be removed. It will be appreciated, however, that great care must be taken in this instance in order to assure that the first implanted assembly 12 and subsequent implanted assemblies 12' are properly disposed relative to each other and to the surrounding articular cartilage and that one side of assembly 12 and one side of an abutting and parallel assembly 12' will serve as a common wall between the two implanted assemblies 12, 12'.

Where two or more assemblies 12, 12' are to be implanted, it is strongly preferred that all of the punching steps be performed prior to the seating of any assembly. This prevents damage to a seated assembly from a punching operation performed adjacent to the already seated assembly Where the area of damaged or destroyed cartilage is so extensive that the bio-absorbable cartilage repair system must include a plurality of the assemblies 12, 12' a rapid and accurate placement of the several assemblies in the appropriate relative locations may be achieved using a jig or spacer 150 according to the present invention. Referring now to FIGS. 15A–15B, the spacer 150 is comprised of a first cannulated (preferably polygonal where the assemblies are polygonal) member 152 having an axis X, N sides, a maximum width (or diameter) W and a length L and a second cannulated (preferably polygonal where the assemblies are polygonal) member 154 having an axis x, n sides, a maximum width (or diameter) w, and a length l. The axes X and x of the first and second cannulated members 152, 154, respectively, are substantially parallel. The number of sides N and the maximum width W of the first cannulated member 152 are at least equal to, and generally exceed, the number of sides n and the maximum width w, respectively, of the second cannulated member 154.

It will be appreciated that one side of the first cannulated member 152 and one side of the second cannulated member 154 are rigidly joined and in effect define a common wall extending at least a portion of the length of the spacer 150. This ensures that the guide wires 120, 120 to be disposed through the cannulae of the spacer 150 will be appropriately positioned in the cancellous bone 74 and that eventually one side of the first assembly 12 will be parallel and contiguous to the adjacent side of the second assembly 12. Typically the first and second cannulated members 152, 154 of the spacer 150 are of integral, one piece, unitary construction formed in a single operation. Where the assembly 12 is polygonal in design, typically the first and second cannulated members 152, 154 will also be polygonal in design.

As best seen in FIG. 15–15B, one end of the first cannulated member and one end of the second cannulated member (the proximal ends as seen in FIG. 15B) are disposed in the same plane, while the opposite end of the first cannulated member 152 and the opposite end of the second cannulated member 154 (the distal ends as seen in FIG. 15A) are disposed in spaced apart parallel planes. More particularly, the distal end of the first cannulated member 152 extends forwardly further than the distal end of the second cannulated member 154, as seen in FIG. 15. This permits the distal end of the first cannulated member 152 to occupy the removed area of destroyed or damaged articulate cartilage 102, while the distal end of the second cannulated member 154 is resting on another portion of damaged or destroyed articulated cartilage 102 (a portion which has not yet been removed and will only be removed after the second guide wire 120 is in place), as illustrated in FIG. 15.

The spacer 150 is used for spacing apart two guide wires 120, 120' during surgical implantation of the second guide wire 120' so that the second guide wire 120' is a fixed distance from the already implanted first guide wire 120. Thus the spacer is used for only a brief portion of the total time of the surgical implantation procedure. More particularly, the first cannulated member 152 of the spacer is passed over the first guide wire 120, with the second cannulated member 154 of the spacer being disposed over another portion of the damaged or destroyed articular cartilage. Once a second guide wire 120' is inserted through the cannula of the second cannulated member 154 of the spacer and the forward tip thereof removeably fixed in cancellous bone 74 (e.g., by power drill 118, as shown in FIG. 15), the spacer 150 is removed from both guide wires 120, 120'. Where the guide wires 120, 120' are resilient, the removal of the spacer 150 may result in the guide wires angling slightly apart at the proximal ends as they attempt to conform with the femoral condyle or other rounded surfaces.

Figure 16:
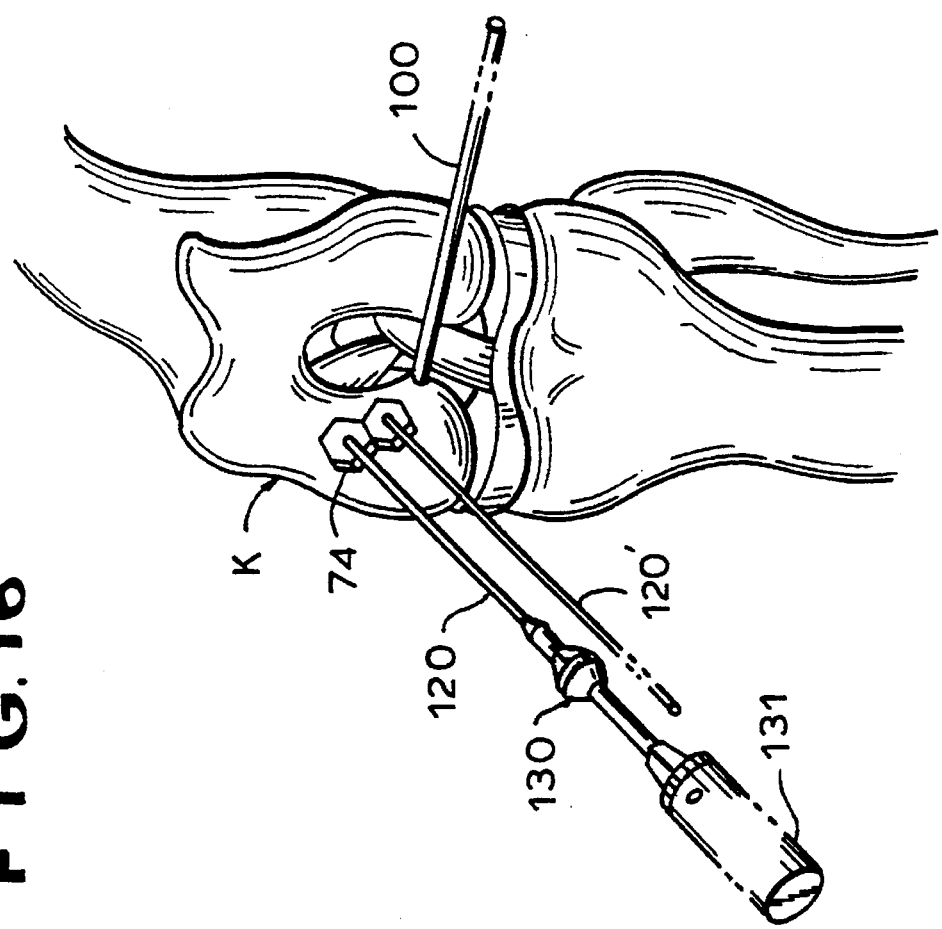
FIG. 16 is a view similar to FIG. 15, but showing the drilling and countersinking of the first assembly after the second guide wire is in place and the spacer removed.

After removal of the spacer 150 from the guide wires 120, 120', a punch 104 is mounted on the second guide wire 120' to remove another portion of the damaged or destroyed articular cartilage 102 and the underlying portion of the subchondral bone plate 72, thereby exposing to view the cancellous bone 74 therebelow. Then all of the procedures described above with regard to first guide wire 120 may be completed prior to any utilization of the second guide wire 120'. Only then are the drill/countersink and seating procedures repeated using the second guide wire 120' (as illustrated in FIG. 16).

Alternatively, work may proceed apace, performing each procedure with each of the guide wires 120, 120' in turn. Thus, in the alternative procedure, after removal of the spacer 150 from guide wires 120, 120', a cannulated punch 104 is passed over the second guide wire 120' and tapped into place. Then cannulated punch 104 is then removed from the second guide wire 120'. Thereafter, cannulated drill/countersinks 130 are in turn placed on each of the guide wires 120, 120', used in the drill/countersink procedures) and then replaced by assemblies 12, 12' for the assembly seating procedures (with impacters 142 and inserters 141 being used if desired to assist in seating the assemblies 12, 12' in turn in their prepared sites prior to removal of the guide wires 120, 120').

Assuming that spacers and assemblies of appropriate configurations and dimensions have been used, the implanted assemblies are not only in the appropriate position relative to one other, but also relative to the periphery of the undamaged articular cartilage surrounding the injury. It is contemplated that the surgeon will have available to him at the time of the operation a plurality of different spacers where the cannulated members vary in configuration and/or dimensions so that the surgeon may select the spacer(s) most appropriate for the particular injury.

To summarize, the present invention provides a method of surgically implanting a system for regenerating articular cartilage, the method being relatively fast and easy to perform even for a surgeon with little experience in this method. The method in one embodiment involving the placement of a plurality of repair assemblies and utilizes apparatus (i.e., a spacer) for determining the appropriate placement of one repair assembly relative to another and facilitates a three dimensional approximation of the original surface of the articular cartilage. The present invention further provides such a spacer.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. A method of surgically implanting, into a site of damaged or destroyed articular cartilage and cancellous bone, a bio-absorbable cartilage repair system including an assembly, the method comprising the steps of:

(A) partially preparing the site to receive the assembly by removing at least a portion of the damaged or destroyed articular cartilage;

(B) removably fixing the forward tip of a guide wire in the cancellous bone under the removed articular cartilage;

(C) utilizing the guide wire to further prepare the site to receive the assembly by drilling and countersinking the subchondral cancellous bone;

(D) utilizing the guide wire to seat the assembly into the and countersunk subchondral cancellous bone until the assembly is flush with the surrounding articular surface; and (E) removing the guide wire.

2. The method of claim 1 wherein in step A the site is partially prepared using a cannulated punch.

3. The method of claim 2 wherein the punch is polygonal.

4. The method of claim 2 wherein in step B the guide wire is inserted through the cannula of the punch after removal of a portion of the damaged or destroyed articular cartilage.

5. The method of claim 1 wherein in step C a cannulated drill/countersink is passed over the guide wire prior to drilling and countersinking.

6. The method of claim 1 wherein in step D the assembly is passed over the guide wire prior to seating.

7. A method of surgically implanting, into a site of damaged or destroyed articular cartilage and cancellous bone, a bio-absorbable cartilage repair system including an assembly adapted to regenerate damaged or destroyed articular cartilage on the surface of a bone by establishing a chondrogenic growth-supporting matrix between an area of damaged or destroyed articular cartilage that has been removed and an adjacent healthy area of articular cartilage and cancellous bone, the assembly including:

(i) a bio-absorbable polygonal delivery unit configured and dimensioned to be mounted in both the removed area and the adjacent healthy area of bone; and (ii) a porous bio-absorbable insert supported by and in the delivery unit and establishing communication between the removed area and the adjacent healthy area for a chondrogenic growth-supporting matrix;

the method comprising the steps of:

(A) partially preparing the site to receive the assembly by removing at least a portion of the damaged or destroyed articular cartilage;

(B) removably fixing the forward tip of a guide wire in the cancellous bone under the removed articular cartilage;

(C) utilizing the guide wire to further prepare the site to receive the assembly by countersinking the subchondral cancellous bone;

(D) utilizing the guide wire to seat the assembly into the countersunk subchondral cancellous bone until the assembly is flush with the surrounding articular surface; and (E) removing the guide wire.

8. A method of surgically implanting a bio-absorbable cartilage repair system having an assembly for regenerating damaged or destroyed articular cartilage on the surface of a bone by establishing a chondrogenic growth-supporting matrix between an area of damaged or destroyed articular cartilage that has been removed and an adjacent healthy area of articular cartilage and cancellous bone, the assembly including:

(i) a bio-absorbable polygonal delivery unit configured and dimensioned to be mounted in both the removed area and the adjacent healthy area of bone; and (ii) a porous bio-absorbable insert supported by and in the delivery unit and establishing communication between the removed area and the adjacent healthy area for a chondrogenic growth-supporting matrix;

the method comprising the steps of:

(A) removing at least a portion of the damaged or destroyed area with a cannulated polygonal punch;

(B) inserting a guide wire through the cannula of the punch and then removably fixing the forward tip thereof in the cancellous bone;

(C) removing the punch from the guide wire;

(D) passing a cannulated countersink over the guide wire and then countersinking the subchondral cancellous bone;

(E) removing the drill/countersink from the guide wire;

(F) passing the assembly over the guide wire and then into the drilled and countersunk subchondral cancellous bone until the assembly is flush with the surrounding articular surface; and (G) removing the guide wire.

9. The method of claim 8 including the preliminary step of inserting an arthroscope adjacent the area of damaged or destroyed articular cartilage to enable viewing of the area.

10. The method of claim 8 including in step B impacting the punch with a mallet until the punch reaches a depth of about 3–4 mm into the articular cartilage and subchondral cancellous bone.

11. The method of claim 8 wherein the guide wire has a self-tapping threaded forward tip and is rotated by a power drill in step D.

12. The method of claim 8 including in step F passing a cannulated inserter and then a cannulated impactor over the guide wire after the assembly and then using the impactor to drive the inserter by itself along the guide wire and against the assembly to seat the assembly in the countersunk subchondral cancellous bone, followed by removing the inserter and impactor from the guide wire.

13. A method of surgically implanting into a site with damaged or destroyed articular cartilage and cancellous bone a bio-absorbable cartilage repair system including at least first and second assemblies, the method comprising the steps of:

(A) proving a spacer for use in spacing apart two guide wires during surgical implantation of the second guide wire a fixed distance from the implanted first guide wire;

(B) partially preparing the site to receive the first assembly by removing at least a portion of the damaged or destroyed articular cartilage;

(C) removably fixing the forward tip of a first guide wire in the cancellous bone under the removed articular cartilage;

(D) utilizing the spacer and the first guide wire to removably fix the forward tip of the second wire guide in the cancellous bone a fixed distance from the first guide wire;

(E) utilizing the second guide wire to partially prepare the site to receive the second assembly by removing another portion of the damaged or destroyed articular cartilage;

(F) utilizing the first and second guide wires to further prepare the site to receive the assembly by countersinking the subchondral cancellous bone;

(G) utilizing the first and second guide wires to seat the first and second assemblies, respectively, into the drilled and countersunk subchondral cancellous bone until the assemblies are flush with the surrounding articular surface; and (H) removing the guide wires.

14. A method of surgically implanting into a site with damaged or destroyed articular cartilage and cancellous bone a bio-absorbable cartilage repair system including at least first and second assemblies, the method comprising the steps of:

(A) proving a spacer for use in spacing apart two guide wires during surgical implantation of the second guide wire a fixed distance from the implanted first guide wire;

(B) partially preparing the site to receive the first assembly by removing at least a portion of the damaged or destroyed articular cartilage;

(C) removably fixing the forward tip of a first guide wire in the cancellous bone under the removed articular cartilage;

(D) utilizing the spacer and the first guide wire to removably fix the forward tip of the second wire guide in the cancellous bone a fixed distance from the first guide wire;

(E) utilizing the second guide wire to partially prepare the site to receive the second assembly by removing another portion of the damaged or destroyed articular cartilage;

(F) utilizing the first and second guide wires to further prepare the site to receive the assembly by and countersinking the subchondral cancellous bone;

(G) utilizing the first and second guide wires to seat the first and second assemblies, respectively, into the countersunk subchondral cancellous bone until the assemblies are flush with the surrounding articular surface; and (H) removing the guide wires;

the spacer including:

(i) a first cannulated polygonal member having an axis X, N sides, a maximum width W and a length L; and (ii) a second cannulated polygonal member having an axis x, n sides, a maximum width w, and a length l, where N, W and L are not less than n, w and l, respectively, and axes X and x are substantially parallel;

one side of said first cannulated member and one side of said second cannulated member being rigidly joined, and one end of said first cannulated member and one end of said second cannulated member being disposed in the same plane, and the opposite end of said first cannulated member and the opposite end of said second cannulated member being disposed in spaced apart parallel planes.

15. The method of claim 14 including the steps of:

(i) passing the first cannulated member of the spacer over the first guide wire with the second cannulated member of the spacer disposed over another portion of the damaged or destroyed articular cartilage area;

(ii) inserting a second guide wire through the cannula of the second cannulated member of the spacer and then removably fixing the forward tip thereof in the cancellous bone; and (iii) removing the spacer from both guide wires.

16. A method of surgically implanting a bio-absorbable cartilage repair system, the method comprising the steps of:

(A) providing at least two assemblies for regenerating damaged or destroyed articular cartilage on the surface of a bone by establishing a chondrogenic growth-supporting matrix between an area of damaged or destroyed articular cartilage that has been removed and an adjacent healthy area of articular cartilage and cancellous bone, each assembly including:
  (i) a bio-absorbable polygonal delivery unit configured and dimensioned to be mounted in both the removed area and the adjacent healthy area of bone; and
  (ii) a porous bio-absorbable insert supported by and in the delivery unit and establishing communication between the removed area and the adjacent healthy area for a chondrogenic growth-supporting matrix;
(B) providing a spacer for use in spacing apart two guide wires during surgical implantation of the second guide wire a fixed distance from the implanted first guide wire, the spacer including
  (i) a first cannulated polygonal member having an axis X, N sides, a maximum width W and a length L; and
  (ii) a second cannulated polygonal member having an axis x, n sides, a maximum width w, and a length l, where N and W are at least equal to n and w, L exceeds l, and axes X and x are substantially parallel;
one side of said first member and one side of said second member being rigidly joined, and one end of said first member and one end of said second member being disposed in the same plane, and the opposite end of said first member and the opposite end of said second member being disposed in spaced apart parallel planes;
(C) removing a portion of the damaged or destroyed area with a cannulated polygonal punch;
(D) inserting a first guide wire through the cannula of the punch and then removably fixing the forward tip thereof in the cancellous bone;
(D) removing the punch from the first guide wire;
(E) passing the first polygonal member of the spacer over the first guide wire with the second polygonal member of the spacer disposed over another portion of the damaged or destroyed area;
(F) inserting a second guide wire through the cannula of the second polygonal member of the spacer and then removably fixing the forward tip thereof in the cancellous bone;

(G) removing the spacer from both guide wires;
(H) passing a cannulated polygonal punch over the second guide wire and then removing the another portion of the damaged or destroyed area;
(I) passing a cannulated countersink over each of the guide wires and then countersinking the subchondral cancellous bone;
(J) removing the countersink from each of the guide wires;
(K) moving each of the assemblies over its respective guide wires and then into the countersunk subchondral cancellous bone until each assembly is flush with the surrounding articular surface; and
(L) removing the guide wires.

17. The method of claim 16 including the preliminary step of inserting an arthroscope adjacent the area of damaged or destroyed articular cartilage to enable viewing of the area.

18. The method of claim 16 including in step C impacting the punch with a mallet until the punch reaches a depth of about 3-4 mm into the articular cartilage and subchondral cancellous bone.

19. The method of claim 16 wherein the guide wire has a self-tapping threaded forward tip and is rotated by a power drill in step D.

20. The method of claim 16 including in step K passing a cannulated inserter and then a cannulated impactor over the guide wire after the assembly and then using the impactor to drive the inserter by itself along the guide wire and against the assembly to seat the assembly in the countersunk subchondral cancellous bone, followed by removing the inserter and impactor from the guide wire.

21. The method of claim 16 wherein in step K the assemblies are moved so that they are in the countersunk subchondral cancellous bone with a planar side surface of one polygonal delivery unit adjacent the planar side surface of another polygonal delivery unit.

* * * * *